(12) United States Patent
Rossi et al.

(10) Patent No.: US 8,946,401 B2
(45) Date of Patent: Feb. 3, 2015

(54) MULTI-TARGETING SHORT INTERFERING RNAS

(75) Inventors: John J. Rossi, Alta Loma, CA (US); Ola Snove, Jr., Oslo (NO); Ali Ehsani, West Covina, CA (US); Pal Saetrom, Trondheim (NO); Britta Hoehn, Hagen (DE); Jane Zhang, South El Monte, CA (US); Lars Aagaard, Ry (DK)

(73) Assignee: City of Hope, Duarte, CA (US)

( * ) Notice: Subject to any disclaimer, the term of this patent is extended or adjusted under 35 U.S.C. 154(b) by 532 days.

(21) Appl. No.: 13/287,493

(22) Filed: Nov. 2, 2011

(65) Prior Publication Data

US 2012/0046343 A1 Feb. 23, 2012

Related U.S. Application Data

(62) Division of application No. 12/021,604, filed on Jan. 29, 2008, now Pat. No. 8,071,752.

(60) Provisional application No. 60/897,844, filed on Jan. 29, 2007, provisional application No. 60/996,849, filed on Dec. 7, 2007.

(51) Int. Cl.
   *C07H 21/04* (2006.01)

(52) U.S. Cl.
   USPC .......................................... 536/24.5; 536/23.1

(58) Field of Classification Search
   None
   See application file for complete search history.

(56) References Cited

U.S. PATENT DOCUMENTS

| | | |
|---|---|---|
| 2004/0053876 A1 | 3/2004 | Turner et al. |
| 2004/0096843 A1 | 5/2004 | Rossi et al. |
| 2006/0025361 A1 | 2/2006 | McSwiggen et al. |
| 2006/0178329 A1 | 8/2006 | Gleave et al. |
| 2009/0192103 A1 | 7/2009 | Rivory et al. |

OTHER PUBLICATIONS

Scherer et al. (Nat. Biotechnol., 2003, 21(12), pp. 1457-1465).*
Zhang et al. (Current Pharmaceutical Biotechnology 2004, vol. 5, p. 1-7).*
Nielsen, Cydney B. et al., "Determinants of targeting by endogenous and exogenous microRNAs and siRNAs," RNA 2007, 13: 1894-1910; © 2007 RNA Society.
Soifer, Harris S. et al., "A potential role for RNA interference in controlling the activity of the human LINE-1 retrotransposon," pp. 846-856, Nucleic Acids Research, 2005, vol. 33, No. 3.
Hossbach, Markus et al., "Gene silencing with siRNA Duplexes Composed of Target-mRNA-Complementary and Partially Palindromic or Partially Complementary Single-Stranded siRNAs," RNA Biology, 2006, vol. 3, Issue 2, pp. 82-89, © Landes Bioscience.
Scacheri, Peter C. et al., "Short interfering RNAs can induce unexpected and divergent changes in the levels of untargeted proteins in mammalian cells," Proc Natl Acad Sci USA, vol. 101, No. 7, pp. 1892-1897, Feb. 17, 2004, © 2004 by The National Academy of Sciences of the USA.
Lee, Nan Sook et al., "Control of HIV-1 replication by RNA interference," Virus Research 102 (2004), pp. 53-58.
Chen, K., "Deep Conservation of microRNA-target Relationships and 3-'UTR Motifs in Vertebrates, Flies, and Nematodes," Cold Spring Harbor Symposia on Quantitative Biology, vol. LXXI, © 2007 Cold Spring Harbor Laboratory Press, pp. 1-8.
Scherer et al., "Approaches for the Sequence-Specific Knockdown of miRNA," 2003, Nat. Biotechnol., 21(12), pp. 1457-1465.
Mahato et al., "Modulation of Gene Expression by Antisense and Antigene Oligodeoxynucleotides and Small Interfering RNA," Jan. 2005, Expert Opinion on Drug Delivery, vol. 2, No. 1, pp. 3-28.
Zhang et al., "Targeted Gene Silencing by Small Interfering RNA-Based Knock-Down Technology," 2004, Current Pharmaceutical Biotechnology, vol. 5, pp. 1-7.
Anderson et al., "Bispecific Short Hairpin siRNA Constructs Targeted to CD4, CXCR4, and CCR5 Confer HIV-1 Resistance," 2003, Oligonucleotides, vol. 13, pp. 303-312.
Leirdal et al., "Gene Silencing in Mammalian Cells by Preformed Small RNA Duplexes," 2002, Biochemical and Biophysical Research Communications, vol. 295, pp. 744-748.
Mangeot et al., "A Universal Transgene Silencing Method Based on RNA Interference," 2004, Nucleic Acids Research, vol. 32, No. 12, pp. 1-6.
Birmingham et al., 3' UTR Seed Matches, But Not Overall Identity, Are Associated with RNAi Off-Targets,: 2006, Nature Methods, vol. 3, No. 3, pp. 199-204.
Jackson et al., "Widespred siRNA "Off-Target" Transcript Silencing Meditated by Seed Region Sequence Complementarily," 2006, RNA, 12 pp. 1179-1187.
Novina et al., "siRNA-Directed Inhibition of HIV-1 Infection,." 2002, Nature Medicine, vol. 8, pp. 681-686.
Doench et al., "siRNAs Can Function as miRNAs," 2003, Genes & Development, 17, pp. 438-442.

\* cited by examiner

*Primary Examiner* — Amy Bowman
(74) *Attorney, Agent, or Firm* — Rothwell, Figg, Ernst & Manbeck P.C.

(57) ABSTRACT

The present invention relates to novel short interfering RNA (siRNA) molecules that are multi-targeted. More specifically, the present invention relates to siRNA molecules that target two or more sequences. In one embodiment, multi-targeting siRNA molecules are designed to incorporate features of siRNA molecules and features of micro-RNA (miRNA) molecules. In another embodiment, multi-targeting siRNA molecules are designed so that each strand is directed to separate targets.

10 Claims, 21 Drawing Sheets

3' UTR target sites

CCR5_1

CCR5_2

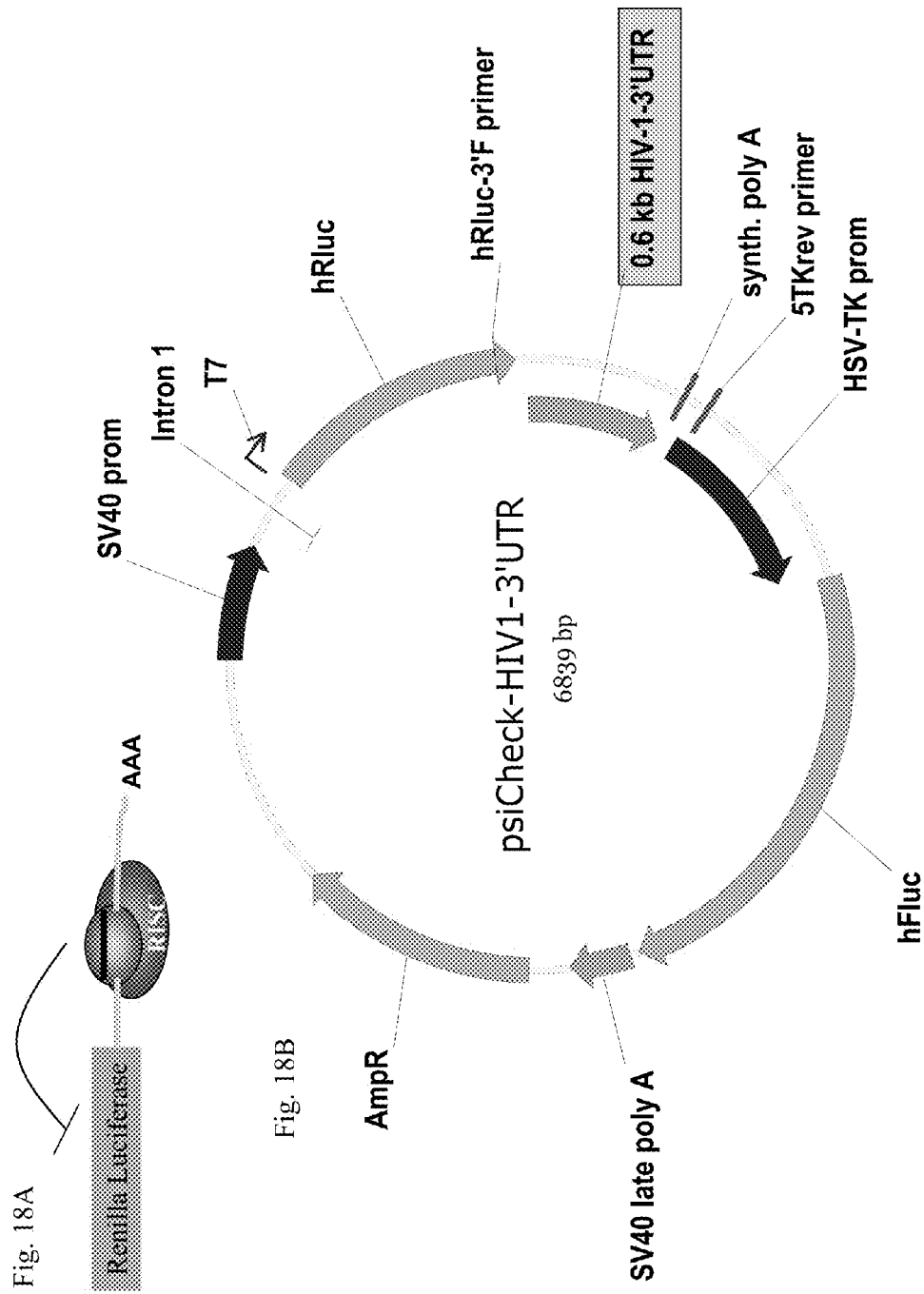

MULTI-TARGETING SHORT INTERFERING RNAS

CROSS-REFERENCE TO RELATED APPLICATION

The present application is a division of U.S. patent application Ser. No. 12/021,604 filed 29 Jan. 2008, which in turn is related to and claims priority under 35 U.S.C. §119(e) to U.S. Provisional Patent Application Ser. No. 60/897,844 filed 29 Jan. 2007 and U.S. Provisional Patent Application Ser. No. 60/996,849 filed 7 Dec. 2007. Each application is incorporated herein by reference.

STATEMENT OF FEDERALLY SPONSORED RESEARCH

The present invention was made in part with Government support under Grant Numbers AI29329, AI42552 and HL07470 awarded by the National Institutes of Health, Bethesda, Md. The Government may have certain rights in this invention.

SEQUENCE SUBMISSION

The present application is being filed along with a Sequence Listing in electronic format. The Sequence Listing is entitled 1954559 SequenceListing.txt, created on 1 Nov. 2011, and is 11 kb in size. The information in the electronic format of the Sequence Listing is part of the present application and is incorporated herein by reference in its entirety.

BACKGROUND OF THE INVENTION

The present invention relates to novel short interfering RNA (siRNA) molecules that are multi-targeted. More specifically, the present invention relates to siRNA molecules that are capable target two or more sequences. In one embodiment, multi-targeting siRNA molecules are designed to incorporate features of siRNA molecules and features of micro-RNA (miRNA) molecules. In another embodiment, multi-targeting siRNA molecules are designed so that each strand is directed to separate targets.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

RNA interference (RNAi) is a process where double-stranded RNA triggers together with protein complexes downregulate mRNA complementary to the triggers (Hannon and Rossi, 2004). The triggers are 19 nt long RNA duplexes with 2 nt 3' overhangs and are referred to as short interfering RNAs (siRNAs). The protein complex, known as the RNA-induced silencing complex (RISC), incorporates one of the siRNA strands and RISC uses this strand as a template to recognize target mRNA. RISC then cleaves mRNA with perfect or near-perfect complementarity to the guide strand. Short interfering RNAs are used as tools to down-regulate specific genes and can either give transient or—when stably integrated as short hairpins RNAs (shRNAs) (Paddison et al., 2002)—stable suppression.

The siRNAs and shRNAs resemble intermediates in the processing pathway of the endogenous microRNA (miRNA) genes (Bartel, 2004). Indeed, siRNAs can function as miR-NAs and vice versa (Zeng et al., 2002; Doench et al., 2003).

MicroRNAs, like siRNAs, use RISC to downregulate target genes, but unlike siRNAs, most animal miRNAs do not cleave the mRNA. Instead, miRNAs reduce protein output through translational suppression or polyA removal and mRNA degradation (Wu et al., 2006). Known miRNA binding sites are within mRNA 3' UTRs; miRNAs seem to target sites with near-perfect complementarity to nucleotides 2-8 from the miRNA's 5' end (Rajewsky, 2006; Lim et al., 2005). This region is known as the seed region. Because siRNAs and miRNAs are interchangeable, exogenous siRNAs will downregulate mRNAs with seed complementarity to the siRNA (Birmingham et al., 2006. Multiple target sites within a 3' UTR give stronger downregulation (Doench et al., 2003).

Although many siRNA molecules have been developed for the treatment of cancer disease, and other conditions, there remains a need for the development of additional new molecules and methods for the RNAi treatment of cancer, disease, and other conditions, particularly the development of new siRNA molecules.

SUMMARY OF THE INVENTION

The present invention relates to novel short interfering RNA (siRNA) molecules that are multi-targeted. More specifically, the present invention relates to siRNA molecules that target two or more sequences. In one embodiment, multi-targeting siRNA molecules are designed to incorporate features of siRNA molecules and features of micro-RNA (miRNA) molecules. In another embodiment, multi-targeting siRNA molecules are designed so that each strand is directed to separate targets.

In one aspect, the present invention provides a new approach for targeting in which an siRNA can target multiple targets. As disclosed herein, this approach is termed "multi-targeting short interfering RNA" or "multi-targeting siRNA." In one embodiment, a multi-targeting siRNA molecule matches a desired coding region sequences, but also contain one or more, preferably at least two, seed matches optimally spaced in the 3' UTR are developed. In this embodiment of the invention, multi-targeting siRNAs use multiple RNA interference (RNAi) pathways to down-regulate their intended target gene, thereby achieving more robust and potent gene down-regulation than tradition siRNAs have. Traditional siRNA are designed to use the cleavage pathway of RNAi only, but siRNAs can also induce miRNA-like translational suppression or polyA degradation and cause transcriptional gene silencing (TGS). siRNAs that combine two or more of these pathways to down-regulate their intended target(s) in accordance with the present invention give more robust down-regulation than siRNAs that rely on only one of the pathways.

In a second embodiment, the present invention provides siRNA molecules in which each strand of the molecule matches different desired coding region sequences. In this embodiment, both strands of the siRNA molecule are functional for the cleavage pathway of RNAi following cleavage by Dicer.

In a second aspect, the present invention provides methods for designing multi-targeting siRNAs of the first embodiment of the first aspect of the present invention. In one embodiment, multi-targeting siRNAs containing siRNA and miRNA functions are designed using the following protocol.

1. Input one mRNA and one 3' UTR target sequence.
2. Identify all 19mer siRNA candidates that have perfect complementarity to the mRNA.

3. For each siRNA candidate, identify miRNA-like target sites within the 3' UTR and remove candidates that have no sites.

4. Use an siRNA efficacy prediction algorithm to identify effective cleavage target sites within the mRNA.

5. Order the siRNA candidates based on predicted miRNA-like down-regulation. This prediction is based on the number of and distance between miRNA-like target sites within the 3' UTR.

In a second embodiment, Step 3 is removed by using siRNAs that are modified such that the guide strand is guaranteed to be preferentially loaded into RISC. Such modifications are well known to the skilled artisan.

In a third aspect, the present invention provides pharmaceutical compositions comprising an effective amount of a multi-targeting siRNA and a pharmaceutically acceptable carrier.

In a fourth aspect, the present invention provides methods for treating a broad spectrum of diseases and conditions, including, but not limited to, cancer or cancerous disease, infectious disease, cardiovascular disease, neurological disease, prion disease, inflammatory disease, autoimmune disease, pulmonary disease, renal disease, liver disease, mitochondrial disease, endocrine disease, reproduction related diseases and conditions, and any other indications that can respond to the level of an expressed gene product in a cell or organism. The term "infectious agent" includes any virus (DNA or RNA virus), bacteria, fungus, or protozoa which is capable of infection.

BRIEF DESCRIPTION OF THE FIGURES

FIG. 1A: A schematic of the multi-targeting siRNA; red illustrates the siRNA "seed" region and green illustrates the rest of the 19mer siRNA guide strand, i.e., the siRNA "cleavage" nucleotides. FIG. 1B: The multi-targeting siRNA can be designed to target one transcript that has one cleavage site somewhere within the mRNA and several seed sites within the 3' UTR; red illustrates the siRNA "seed" region and green illustrates the rest of the 19mer siRNA guide strand, i.e., the siRNA "cleavage" nucleotides. FIG. 1C: Alternatively, the multi-targeting siRNA can be designed to have a cleavage site within one mRNA and several seed sites within the 3' UTR of another transcript; red illustrates the siRNA "seed" region and green illustrates the rest of the 19mer siRNA guide strand, i.e., the siRNA "cleavage" nucleotides.

FIG. 16A: After binding of the Dicer protein to the Dicer-substrate duplex (top center) the duplex is processed to siRNA and therefore the two strands of the duplex are incorporated into different RISCs. The lower left diagram depicts the incorporation of the anti-CCR5 (red line) strand into RISC and cleavage of the target mRNA (green line). The lower right diagram depicts incorporation of the U2 miRNA (black line) into RISC and translational inhibition of HIV proteins. FIG. 16B depicts the U2 and CCR5 strands against their targets. There are two seed sequences with optimal distance (36 nt.) in the HIV (expressed from the pNL4-3 plasmid) 3' UTR that the U2 strand can bind to and exhibit miRNA activity. The bottom strand of the multifunctional siRNA targets the CCR5 mRNA coding region with perfect complementarity.

FIG. 17A: Structure of the U2 miRNA bound to the first HIV 3' UTR site starting at nucleotide 362 of the 3'UTR. FIG. 17B: Structure of the U2 miRNA bound to the second HIV 3' UTR site starting at nucleotide 398 of the 3'UTR.

FIGS. 18A and 18B show a schematic of the reporter pU. FIG. 18A: Translational inhibition of the Renilla Luciferase gene by incorporation of the U2 miRNA into the RISC. FIG. 18B: The psiCheck reporter construct engineered to express the HIV 3'UTR downstream of the Renilla coding region.

FIG. 19A: mRNA cleavage of the Renilla Luciferase gene by incorporation of anti-CCR5 siRNA into the RISC. FIG. 19B: The psiCheck reporter construct engineered to express one kilo-bases of the CCR5 coding sequence downstream of the Renilla coding region.

DETAILED DESCRIPTION OF THE INVENTION

Figure 1A:
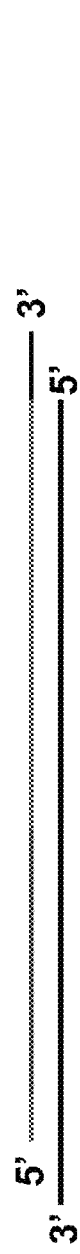
FIGS. 1A-1C show multi-targeting siRNAs that combine cleavage and translational inhibition.
Figure 1B:
Figure 1C:
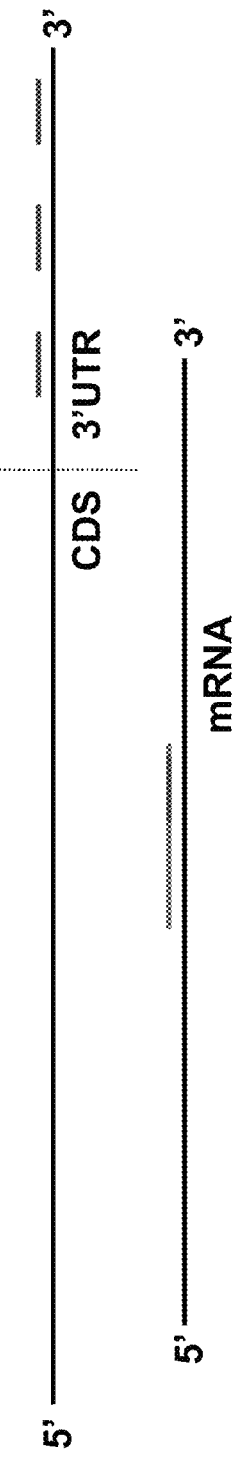

The present invention relates to novel short interfering RNA (siRNA) molecules that are multi-targeted. A multi-targeting siRNA may be directed against a single target gene or target sequence or may be directed against multiple targets or target sequences. In one embodiment, multi-targeting siRNA molecules are designed to incorporate features of siRNA molecules and features of micro-RNA (miRNA) molecules. In another embodiment, multi-targeting siRNA molecules are designed so that each strand is directed to separate targets.

The term "short interfering RNA" or "siRNA" as used herein refers to any nucleic acid molecule capable of inhibiting or down regulating gene expression or viral replication, for example by mediating RNA interference "RNAi" or gene silencing in a sequence-specific manner.

As used herein, the term "microRNA" or "miRNA" refers to any type of interfering RNA, including but not limited to, endogenous miRNA and artificial miRNA. Endogenous miRNA are small RNAs naturally present in the genome which are capable of modulating the productive utilization of mRNA. The term artificial miRNA includes any type of RNA sequence, other than endogenous miRNA, which is capable of modulating the productive utilization of mRNA.

As used herein, "target gene" includes any nucleotide sequence, which may or may not contain identified gene(s), including, without limitation, intergenic region(s), non-coding region(s), untranscribed region(s), intron(s), exon(s), and transgene(s). The target gene can be a gene derived from a cell, an endogenous gene, a transgene, or exogenous genes such as genes of a pathogen, for example a virus, which is present in the cell after infection thereof. The cell containing the target gene can be derived from or contained in any organism By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (i.e., multi-target siRNA) of the invention. In one embodiment, inhibition, down-regulation or reduction with a multi-target siRNA molecule is below that level observed in the presence of an inactive or attenuated molecule. In another embodiment, inhibition, down-regulation, or reduction with multi-target siRNA molecules is below that level observed in the presence of, for example, a multi-target siRNA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "sense region" is meant a nucleotide sequence of a multi-target siRNA molecule having complementarity to an antisense region of the multi-target siRNA molecule. In addition, the sense region of a multi-target siRNA molecule can comprise a nucleic acid sequence having homology with a target nucleic acid sequence.

By "antisense region" is meant a nucleotide sequence of a multi-target siRNA molecule having complementarity to a target nucleic acid sequence. In addition, the antisense region of a multi-target siRNA molecule can optionally comprise a nucleic acid sequence having complementarity to a sense region of the multi-target siRNA molecule.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells.

The functional definitions of miRNAs and siRNAs are based upon their target site interactions and mechanism of action in altering gene expression. miRNAs serve as guides for identifying short sequences (as few as 7 bases), most often in the 3' UTR to which they base pair and posit their associated argonaute and associated factors for translational inhibition. The base pairing region of miRNAs is called the "seed" sequence, usually consisting of bases 2-8 from the 5' end of the antisense guide. Additional base pairing can take place, but only the seed sequence need pair to have functionality. siRNAs function via complete or near complete complementarity with their target sites, which can be anywhere on the message. They usually program Argonaute 2, which contains a cleavage domain, to cleave the target sequence between bases 10 and 11 relative to the 5' end of the antisense strand of the siRNA (reviewed in Filipowicz et al., 2005; Kim, 2005). The binding of miRNAs to the 3' UTR can also trigger degradation, but this is not initiated by site specific cleavage of the target, but appears to be a function of the inclusion of the miRNA/mRNA complex in processing bodies, or P-bodies (Liu et al., 2005).

In our studies of the genomic distribution of distances between pairs of identical miRNA seeds, we have found a propensity for moderate distances greater than 13 nucleotides between seed starts. Experimental data showed that optimal downregulation is obtained when two seed sites are separated by between 13 and 35 nucleotides, but can still be effective even when they are 100 bases apart (Saetrom et al., 2007). These findings are useful in developing improved miRNA target prediction algorithms, as we have now incorporated the concept of sub-optimal versus optimal spacings between sites as a predictor of efficacy. Very potent targets are likely to result in multiple miRNA-containing complexes binding within a narrowly defined region of the target to optimize functional interaction. To illustrate, there are 12,735 non-overlapping conserved pairs of hexamer seed sites throughout human 3' UTRs for the miRNAs in version 8.0 of miRBase (Griffiths-Jones et al., 2006), but only 2,257 pairs which are separated by more than 13 and less than 100 nucleotides. Our results also indicate that multiple co-expressed miRNAs will cooperate to down-regulate targets that contain multiple consecutive optimally spaced seed sites.

By analyzing the distance between seed sites of endogenous miRNAs and transfected siRNAs, we also find that cooperative targeting of sites with a separation in the optimal range can explain some of the siRNA off-target effects that have been reported in the literature, since siRNAs can function as miRNAs when they have a seed match in the 3' UTR of a non-targeted message (Jackson et al., 2006). This off-targeting may be enhanced when they bind within the optimal distance from an endogenous miRNA. That is, our results indicate that siRNA off-targeting is related to cooperative downregulation by endogenous miRNAs.

Thus, and in accordance with one aspect of the present invention, a new approach for targeting is provided in which an siRNA molecule targets multiple targets. As disclosed herein, this approach is termed "multi-targeting short interfering RNA" or "multi-targeting siRNA." In one embodiment, a multi-targeting siRNA molecule matches a desired coding region sequences, but also contain one or more, preferably at least two, seed matches optimally spaced in the 3' UTR are developed. In this embodiment of the invention, the multi-targeting siRNAs use multiple RNA interference (RNAi) pathways to down-regulate their intended target gene, thereby achieving more robust and potent gene downregulation than tradition siRNAs have. Traditional siRNA are designed to use the cleavage pathway of RNAi only, but siRNAs can also induce miRNA-like translational suppression or polyA degradation and cause transcriptional gene silencing (TGS). siRNAs that combine two or more of these pathways to down-regulate their intended target(s) in accordance with the present invention give more robust down-regulation than siRNAs that rely on only one of the pathways.

This embodiment of the present invention currently focuses on combining the cleavage and miRNA-targeting pathways. We discovered that the distance between multiple miRNA-like target sites dictates the down-regulation, and we have used this result to create rules for designing siRNAs that give potent miRNA-like down-regulation combined with "traditional" mRNA cleavage. In theory, the approach can, however, also be combined with TGS to, for example, create siRNAs that cause TGS, mRNA cleavage, and miRNA-like down-regulation. Note that our "distance rules" also holds for target sites from different siRNAs, such that we can use these rules to design different siRNAs that, if jointly introduced in the cell, cooperatively down-regulates the intended target. This embodiment of the present invention adds another layer of robustness to our approach.

The present invention is not limited to target single genes. In some instances, one can achieve more robust down-regulation of the intended target by targeting additional genes, such as for example transcription factors that positively regulate the intended target. It may not be possible to find a cleavage site that is common for the two (or more) intended targets, but our approach gives the possibility to target one gene with one RNAi pathway (such as cleavage) and the other gene with another pathway (such as miRNA-like targeting).

In summary, we know that siRNAs can use two mechanisms to target mRNAs for downregulation. The cleavage mechanism is normally the desired mechanism, whereas the "miRNA-like" downregulation is an undesirable off-target effect. However, the present invention relates to the design of siRNAs that use both mechanisms to target specific mRNAs. More specifically, when designing siRNAs that target a specific mRNA, we ensure that 1) the siRNA has a perfectly complementary target site within the mRNA and 2) the siRNA has several miRNA-like target sites within the mRNA's 3' UTR and that these target sites preferably are within the distance interval for optimal down-regulation.

In a second embodiment, multi-targeting siRNA molecules are provided in which each strand of the molecule matches different desired coding region sequences. In this embodiment, both strands of the siRNA molecule are functional for the cleavage pathway of RNAi following cleavage by Dicer. In this embodiment, it is possible to target two different genes with the cleavage RNAi pathway.

In one embodiment, multi-targeting siRNAs are designed using the following protocol.

1. Input one mRNA and one 3' UTR target sequence.
2. Identify all 19mer siRNA candidates that have perfect complementarity to the mRNA.
3. For each siRNA candidate, identify miRNA-like target sites within the 3' UTR and remove candidates that have no sites.
4. Use an siRNA efficacy prediction algorithm to identify effective cleavage target sites within the mRNA.
5. Order the siRNA candidates based on predicted miRNA-like down-regulation. This prediction is based on the number of and distance between miRNA-like target sites within the 3' UTR.

In another embodiment, Step 3 is removed by using siRNAs that are modified such that the guide strand is guaranteed to be preferentially loaded into RISC. Such modifications are well known to the skilled artisan.

In an additional embodiment, mRNA cleavage is incorporated into multi-targeting siRNAs. For example, siRNAs have been designed where both strands have perfect complementarity to mRNA and can cause mRNA cleavage (Hossbach et al., 2006). This design can be incorporated in the multi-targeting siRNAs of the present invention such that both strands can induce cleavage and have multiple miRNA-like target sites within the target 3' UTR.

siRNA efficacy prediction algorithms are well known to the skilled artisan. Such algorithms include those described and referenced in Vert et al., 2006: Heale et al., 2005; Saetrom and Snove, 2004; Saetrom, 2004; Chalk et al., 2004). Any suitable siRNA efficacy prediction algorithm can be used in the present invention.

The siRNA molecules of the invention represent a novel therapeutic approach to a broad spectrum of diseases and conditions, including, but not limited to, cancer or cancerous disease, infectious disease, cardiovascular disease, neurological disease, prion disease, inflammatory disease, autoimmune disease, pulmonary disease, renal disease, liver disease, mitochondrial disease, endocrine disease, reproduction related diseases and conditions, and any other indications that can respond to the level of an expressed gene product in a cell or organism. The term "infectious agent" includes any virus (DNA or RNA virus), bacteria, fungus, or protozoa which is capable of infection.

In one embodiment, and for illustrative purposes only, multi-targeting siRNAs to achieve robust down-regulation of HIV are prepared. We use two "multi-targeting" strategies to target HIV. In one embodiment, we have siRNAs that have a cleavage site in a HIV coding region and miRNA-like sites in the 3' HIV UTR. In a second embodiment, we have siRNAs that have a cleavage site in CCR5—a co-receptor for HIV to enter host cells—and miRNA-like sites in the 3' HIV UTR. In the first embodiment, the miRNA-like target sites in the 3' UTR ensures that any mRNA not cleaved by the siRNA instead gets down-regulated by the "miRNA"-pathway. It also gives robustness against escape mutants, as the virus must have mutations in both the cleavage and miRNA-like sites to escape siRNA down-regulation and propagate. In the second embodiment, the cleavage sites in CCR5 prevent HIV integration and the miRNA-like sites in the HIV 3' UTR serves as a backup to down-regulate any virus that should enter the cell.

As described above, the major objective in using this approach for HIV is to minimize viral escape mutants. Thus, if mutations arise in the coding region, abrogating the effect of the siRNA, the siRNA can still function as a miRNA by interacting with sites in the 3' UTR suppress viral protein expression and even promote P-body associated degradation by this mechanism. Of course the same is true for a mutation in the 3' UTR, which may abrogate the potency of the miR-NAs but the siRNA can still function.

In another embodiment, and for illustrative purposes only, multi-targeting siRNAs to achieve robust down-regulation of Non-Hodgkin's lymphomas (NHLs) are prepared. NHLs comprise a group of heterogeneous lymphoid malignancies for which conventional chemo- and radiotherapy approaches are rarely curative and many lymphomas relapse within the first year. One hallmark of many types of B-cell lymphomas is the constitutive expression of oncogenes such as the transcription factors Bcl6, STAT3 and cMyc and the anti-apoptotic protein Bcl2. Over expression of these genes causes uncontrolled proliferation, survival of malignant cells and protection against ionizing radiation and many commonly used chemotherapeutics, making knockdown of these genes by RNA interference (RNAi) a rational strategy for therapeutic intervention. RNAi is a conserved endogenous mechanism in which small interfering RNAs (siRNAs) suppress target-specific gene expression by promoting mRNA degradation.

We have designed potent Dicer-substrate siRNAs that show improved efficacy at lower concentrations compared with conventional 21mer siRNAs. In addition we have designed bifunctional siRNA duplexes that provide two guide strands simultaneously suggesting the reduction of effective drug concentration, lower production costs, and decrease of off-target effects compared to conventional siRNAs.

In addition, the present invention provides a method for treating diseases. The molecules of the present invention are administered to patients in need of treatment using conventional pharmaceutical practices or as described herein. Suitable pharmaceutical practices are described in *Remington: The Science and Practice of Pharmacy*, 21$^{st}$ Ed., University of Sciences in Philadelphia, Ed., Philadelphia, 2005.

The siRNA molecule may have different forms, including a single strand, a paired double strand (dsRNA) or a hairpin (shRNA) and can be produced, for example, either synthetically or by expression in cells. In one embodiment, DNA sequences for encoding the sense and antisense strands of the siRNA molecule to be expressed directly in mammalian cells can be produced by methods known in the art, including but not limited to, methods described in U.S. published application Nos. 2004/0171118 A1, 2005/0244858 A1 and 2005/0277610 A1, each incorporated herein by reference. The siRNA molecules are coupled to carrier molecules, such as CpG oligodeoxynucleotides using the techniques described in U.S. provisional patent application Ser. No. 60/897,495 filed 26 Jan. 2007, U.S. patent application Ser. No. 11/966,423 filed 28 Dec. 2007 and International patent application No. PCT/US2007/026432 filed 28 Dec. 2007, each incorporated herein by reference.

In one aspect, DNA sequences encoding a sense strand and an antisense strand of a siRNA specific for a target sequence of a gene are introduced into mammalian cells for expression. To target more than one sequence in the gene (such as different promoter region sequences and/or coding region sequences), separate siRNA-encoding DNA sequences specific to each targeted gene sequence can be introduced simultaneously into the cell. In accordance with another embodiment, mammalian cells may be exposed to multiple siRNAs that target multiple sequences in the gene.

The siRNA molecules generally contain about 19 to about 30 base pairs, and preferably are designed to cause methylation of the targeted gene sequence. In one embodiment, the siRNA molecules contain about 19-23 base pairs, and preferably about 21 base pairs. In another embodiment, the siRNA molecules contain about 24-28 base pairs, and preferably about 26 base pairs. In a further embodiment, the dsRNA has an asymmetric structure, with the sense strand having a 25-base pair length, and the antisense strand having a 27-base pair length with a 2 base 3'-overhang. See, for example, U.S. published application Nos. 2005/0244858 A1 and 2005/0277610 A1, each incorporated herein by reference. In another embodiment, this dsRNA having an asymmetric structure further contains 2 deoxynucleotides at the 3' end of the sense strand in place of two of the ribonucleotides. Individual siRNA molecules also may be in the form of single strands, as well as paired double strands ("sense" and "antisense") and may include secondary structure such as a hairpin loop. Individual siRNA molecules could also be delivered as precursor molecules, which are subsequently altered to give rise to active molecules. Examples of siRNA molecules in the form of single strands include a single stranded anti-sense siRNA against a non-transcribed region of a DNA sequence (e.g. a promoter region).

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3' end of antisense strand and are sufficiently complementary to a nucleotide sequence of the RNA produced from the target gene.

The precursor RNAi molecule, may also have one or more of the following additional properties: (a) the antisense strand has a right shift from the typical 21mer and (b) the strands may not be completely complementary, i.e., the strands may contain simple mismatch pairings. A "typical" 21mer siRNA is designed using conventional techniques, such as described above. This 21mer is then used to design a right shift to include 1-7 additional nucleotides on the 5' end of the 21mer. The sequence of these additional nucleotides may have any sequence. Although the added ribonucleotides may be complementary to the target gene sequence, full complementarity between the target sequence and the siRNA is not required. That is, the resultant siRNA is sufficiently complementary with the target sequence. The first and second oligonucleotides are not required to be completely complementary. They only need to be substantially complementary to anneal under biological conditions and to provide a substrate for Dicer that produces a siRNA sufficiently complementary to the target sequence. In one embodiment, the dsRNA has an asymmetric structure, with the antisense strand having a 25-base pair length, and the sense strand having a 27-base pair length with a 2 base 3'-overhang. In another embodiment, this dsRNA having an asymmetric structure further contains 2 deoxynucleotides at the 3' end of the antisense strand.

Suitable dsRNA compositions that contain two separate oligonucleotides can be linked by a third structure. The third structure will not block Dicer activity on the dsRNA and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the dsRNA is a manner such that a hairpin structure is produced upon annealing of the two oligonucleotides making up the dsRNA composition. The hairpin structure will not block Dicer activity on the dsRNA and will not interfere with the directed destruction of the RNA transcribed from the target gene.

The sense and antisense sequences may be attached by a loop sequence. The loop sequence may comprise any sequence or length that allows expression of a functional siRNA expression cassette in accordance with the invention. In a preferred embodiment, the loop sequence contains higher amounts of uridines and guanines than other nucleotide bases. The preferred length of the loop sequence is about 4 to about 9 nucleotide bases, and most preferably about 8 or 9 nucleotide bases.

In another embodiment of the present invention, the dsRNA, i.e., the precursor RNAi molecule, has several properties which enhances its processing by Dicer. According to this embodiment, the dsRNA has a length sufficient such that it is processed by Dicer to produce an siRNA and at least one of the following properties: (i) the dsRNA is asymmetric, e.g., has a 3' overhang on the sense strand and (ii) the dsRNA has a modified 3' end on the antisense strand to direct orientation of Dicer binding and processing of the dsRNA to an active siRNA. According to this embodiment, the longest strand in the dsRNA comprises 24-30 nucleotides. In one embodiment, the sense strand comprises 24-30 nucleotides and the antisense strand comprises 22-28 nucleotides. Thus, the resulting dsRNA has an overhang on the 3' end of the sense strand. The overhang is 1-3 nucleotides, such as 2 nucleotides. The antisense strand may also have a 5' phosphate.

Modifications can be included in the dsRNA, i.e., the precursor RNAi molecule, so long as the modification does not prevent the dsRNA composition from serving as a substrate for Dicer. In one embodiment, one or more modifications are made that enhance Dicer processing of the dsRNA. In a second embodiment, one or more modifications are made that result in more effective RNAi generation. In a third embodiment, one or more modifications are made that support a greater RNAi effect. In a fourth embodiment, one or more modifications are made that result in greater potency per each dsRNA molecule to be delivered to the cell. Modifications can be incorporated in the 3'-terminal region, the 5'-terminal region, in both the 3'-terminal and 5'-terminal region or in some instances in various positions within the sequence. With the restrictions noted above in mind any number and combination of modifications can be incorporated into the dsRNA. Where multiple modifications are present, they may be the same or different. Modifications to bases, sugar moieties, the phosphate backbone, and their combinations are contemplated. Either 5'-terminus can be phosphorylated.

In another embodiment, the antisense strand is modified for Dicer processing by suitable modifiers located at the 3' end of the antisense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is an asymmetric composition with DNA on the blunt end and RNA bases on the overhanging end.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1, each incorporated herein by reference. Other modifications are disclosed in Herdewijn (2000), Eckstein (2000), Rusckowski et al. (2000), Stein et al. (2001) and Vorobjev et al. (2001), each incorporated herein by reference.

Additionally, the siRNA structure can be optimized to ensure that the oligonucleotide segment generated from Dicer's cleavage will be the portion of the oligonucleotide that is most effective in inhibiting gene expression. For example, in one embodiment of the invention a 27-bp oligonucleotide of the dsRNA structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand.

RNA may be produced enzymatically or by partial/total organic synthesis, and modified ribonucleotides can be introduced by in vitro enzymatic or organic synthesis. In one embodiment, each strand is prepared chemically. Methods of synthesizing RNA molecules are known in the art, in particular, the chemical synthesis methods as described in Verma and Eckstein (1998).

In another aspect, the present invention provides for a pharmaceutical composition comprising the siRNA of the present invention. The siRNA sample can be suitably formulated and introduced into the environment of the cell by any means that allows for a sufficient portion of the sample to enter the cell to induce gene silencing, if it is to occur. Many formulations for dsRNA are known in the art and can be used so long as siRNA gains entry to the target cells so that it can act. See, e.g., U.S. published patent application Nos. 2004/0203145 A1 and 2005/0054598 A1, each incorporated herein by reference. For example, siRNA can be formulated in buffer solutions such as phosphate buffered saline solutions, liposomes, micellar structures, and capsids. Formulations of siRNA with cationic lipids can be used to facilitate transfection of the dsRNA into cells. For example, cationic lipids, such as lipofectin (U.S. Pat. No. 5,705,188, incorporated herein by reference), cationic glycerol derivatives, and polycationic molecules, such as polylysine (published PCT International Application WO 97/30731, incorporated herein by reference), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

It can be appreciated that the method of introducing siRNA into the environment of the cell will depend on the type of cell and the make up of its environment. For example, when the cells are found within a liquid, one preferable formulation is with a lipid formulation such as in lipofectamine and the siRNA can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate siRNA in a buffer or saline solution and directly inject the formulated dsRNA into cells, as in studies with oocytes. The direct injection of dsRNA duplexes may also be done. For suitable methods of introducing siRNA see U.S. published patent application No. 2004/0203145 A1, incorporated herein by reference. In a further embodiment, the siRNA is delivered by a carrier molecule such as CpG oligodeoxynucleotides as described in provisional patent application Ser. No. 60/897,495, filed 26 Jan. 2007, incorporated herein by reference.

Suitable amounts of siRNA must be introduced and these amounts can be empirically determined using standard methods. Typically, effective concentrations of individual siRNA species in the environment of a cell will be about 50 nanomolar or less 10 nanomolar or less, or compositions in which concentrations of about 1 nanomolar or less can be used. In other embodiment, methods utilize a concentration of about 200 picomolar or less and even a concentration of about 50 picomolar or less can be used in many circumstances.

The method can be carried out by addition of the siRNA compositions to any extracellular matrix in which cells can live provided that the siRNA composition is formulated so that a sufficient amount of the siRNA can enter the cell to exert its effect. For example, the method is amenable for use with cells present in a liquid such as a liquid culture or cell growth media, in tissue explants, or in whole organisms, including animals, such as mammals and especially humans.

Expression of a target gene can be determined by any suitable method now known in the art or that is later developed. It can be appreciated that the method used to measure the expression of a target gene will depend upon the nature of the target gene. For example, when the target gene encodes a protein the term "expression" can refer to a protein or transcript derived from the gene. In such instances the expression of a target gene can be determined by measuring the amount of mRNA corresponding to the target gene or by measuring the amount of that protein. Protein can be measured in protein assays such as by staining or immunoblotting or, if the protein catalyzes a reaction that can be measured, by measuring reaction rates. All such methods are known in the art and can be used. Where the gene product is an RNA species expression can be measured by determining the amount of RNA corresponding to the gene product. The measurements can be made on cells, cell extracts, tissues, tissue extracts or any other suitable source material.

The determination of whether the expression of a target gene has been reduced can be by any suitable method that can reliably detect changes in gene expression. Typically, the determination is made by introducing into the environment of a cell undigested siRNA such that at least a portion of that siRNA enters the cytoplasm and then measuring the expression of the target gene. The same measurement is made on identical untreated cells and the results obtained from each measurement are compared.

The siRNA can be formulated as a pharmaceutical composition which comprises a pharmacologically effective amount of a siRNA and pharmaceutically acceptable carrier. A pharmacologically or therapeutically effective amount refers to that amount of a siRNA effective to produce the intended pharmacological, therapeutic or preventive result. The phrases "pharmacologically effective amount" and "therapeutically effective amount" or simply "effective amount" refer to that amount of a RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA composition may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general a suitable dosage unit of siRNA will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the siRNA can be administered once daily. However, the therapeutic agent may also be dosed in dosage units containing two, three, four, five, six or more sub-doses administered at appropriate intervals throughout the day. In that case, the siRNA contained in each sub-dose must be correspondingly smaller in order to achieve the total daily dosage unit. The dosage unit can also be compounded for a single dose over several days, e.g., using a conventional sustained release formulation which provides sustained and consistent release of the siRNA over a several day period. Sustained release formulations are well known in the art. In this embodiment, the dosage unit contains a corresponding multiple of the daily dose. Regardless of the formulation, the pharmaceutical composition must contain siRNA in a quantity sufficient to inhibit expression of the target gene in the animal or human being treated. The composition can be compounded in such a way that the sum of the multiple units of siRNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

In a further aspect, the present invention relates to a method for TGS in a mammalian, including human, cell. The method comprises introducing the siRNA into the appropriate cell. The term "introducing" encompasses a variety of methods of introducing DNA into a cell, either in vitro or in vivo. Such methods include transformation, transduction, transfection, and infection. Vectors are useful and preferred agents for introducing DNA encoding the siRNA molecules into cells. The introducing may be accomplished using at least one vector. Possible vectors include plasmid vectors and viral vectors. Viral vectors include retroviral vectors, lentiviral vectors, or other vectors such as adenoviral vectors or adeno-associated vectors. In one embodiment, the DNA sequences are included in separate vectors, while in another embodiment, the DNA sequences are included in the same vector. The DNA sequences may be inserted into the same vector as a multiple cassettes unit. Alternate delivery of siRNA molecules or DNA encoding siRNA molecules into cells or tissues may also be used in the present invention, including liposomes, chemical solvents, electroporation, viral vectors, pinocytosis, phagocytosis and other forms of spontaneous or induced cellular uptake of exogenous material, as well as other delivery systems known in the art. In a further embodiment, the siRNA is delivered by a carrier molecule such as CpG oligodeoxynucleotides or RNA aptamers as described in further detail herein.

Suitable promoters include those promoters that promote expression of the interfering RNA molecules once operatively associated or linked with sequences encoding the RNA molecules. Such promoters include cellular promoters and viral promoters, as known in the art. In one embodiment, the promoter is an RNA Pol III promoter, which preferably is located immediately upstream of the DNA sequences encoding the interfering RNA molecule. Various viral promoters may be used, including, but not limited to, the viral LTR, as well as adenovirus, SV40, and CMV promoters, as known in the art.

In one embodiment, the invention uses a mammalian U6 RNA Pol III promoter, and more preferably the human U6snRNA Pol III promoter, which has been used previously for expression of short, defined ribozyme transcripts in human cells (Bertrand et al., 1997; Good et al., 1997). The U6 Pol III promoter and its simple termination sequence (four to six uridines) were found to express siRNAs in cells. Appropriately selected interfering RNA or siRNA encoding sequences can be inserted into a transcriptional cassette, providing an optimal system for testing endogenous expression and function of the RNA molecules.

In a further aspect, the invention provides a method for TGS in a mammalian, including human, cell comprising introducing into the cell DNA sequences encoding a sense strand and an antisense strand of an siRNA, which is specific for a target sequence in the gene to be silenced, preferably under conditions permitting expression of the siRNA in the cell, and wherein the siRNA directs methylation of said gene of interest. In an embodiment, methylation is directed to a sequence in the promoter region of the gene. Alternately, methylation is directed to a sequence in the coding region. Target sequences can be any sequence in a gene that has the potential for methylation. In a preferred embodiment, the target sequences may contain CpG islands. The directed methylation can lead to inactivation of the gene. To target more than one sequence in the gene (such as different promoter region sequences and/or coding region sequences), separate siRNA-encoding DNA sequences specific to each targeted gene sequence can be introduced simultaneously into the cell. In addition, cells may be exposed to multiple siRNAs that target multiple sequences in the gene.

Once a target sequence or sequences have been identified for methylation in accordance with the invention, the appropriate siRNA can be produced, for example, either synthetically or by expression in cells. In a one embodiment, the DNA sequences encoding the sense and antisense strands of the siRNA molecule can be generated by PCR. In another embodiment, the siRNA encoding DNA is cloned into a vector, such as a plasmid or viral vector, to facilitate transfer into mammals. In another embodiment, siRNA molecules may be synthesized using chemical or enzymatic means.

To facilitate nuclear retention and increase the level of methylation, the sense and antisense strands of the siRNA molecule may be expressed in a single stranded form, for example as a stem loop structure, as described above. Alternatively, or in concomitance, the factor(s) involved in the active cellular transport of siRNA's, such as Exportin 5, may be downregulated employing synthetic siRNA, antisense, ribozymes, or any other nucleic acid, antibody or drug, proven to be effective in downregulating the gene(s) of interest.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-V C H, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004; Clarke and Sanseau, *microRNA: Biology, Function & Expression* (Nuts & Bolts series), DNA Press, 2006.

EXAMPLES

The present invention is described by reference to the following Examples, which are offered by way of illustration and are not intended to limit the invention in any manner. Standard techniques well known in the art or the techniques specifically described below were utilized.

Example 1 siRNAs Targeting HIV pNL4-3 Strain and CCR5 Gene

We have designed and tested multi-targeting siRNAs that target the HIV pNL4-3 strain (Table 1) and the CCR5 gene (Table 2), which is a co-receptor for HIV to enter host cells. All siRNAs have miRNA-like target sites within HIV 3' UTR, but the cleavage target varies for the different siRNAs. We designed the CCR5 siRNAs (Table 2) such that their 3' UTR sites have near-optimal distances to the HIV-targeting siRNAs (Table 1). These siRNAs give optimal cooperative miRNA-like targeting of the 3' UTR when jointly introduced in the cell. The effects of these multi-targeting siRNAs on pNL4-3 are shown in FIGS. 7-11.

TABLE 1 siRNAs Designed Against pNL4-3 gag-pol and 3' UTR

| ID | Sense (SEQ ID NO:) 5'-3' | Antisense (SEQ ID NO:) 3'-5' | CDS site | 3' UTR sites | Dist |
|---|---|---|---|---|---|
| CU3 | ucaggaaguauacugcauu (1) | aaugcaguauacuuccuga (2) | 2132 | 219, 303, 422 | 84, 119 |
| CU2 | gagcuucagguuugggaa (3) | uuccccaaaccugaagcuc (4) | 1384 | 362, 398 | 36 |

TABLE 1-continued siRNAs Designed Against pNL4-3 gag-pol and 3' UTR

| ID | Sense (SEQ ID NO:) 5'-3' | Antisense (SEQ ID NO:) 3'-5' | CDS site | 3' UTR sites | Dist |
|---|---|---|---|---|---|
| U2 | uggacuuuugacuggggaa (5) | uuccccagucaaaagucca (6) | None | 362, 398 | 36 |
| P2 | uuccccauuuagugggaa (7) | uuccccacuaaauggggaa (8) | None | 362, 398 | 36 |

Figure 2:
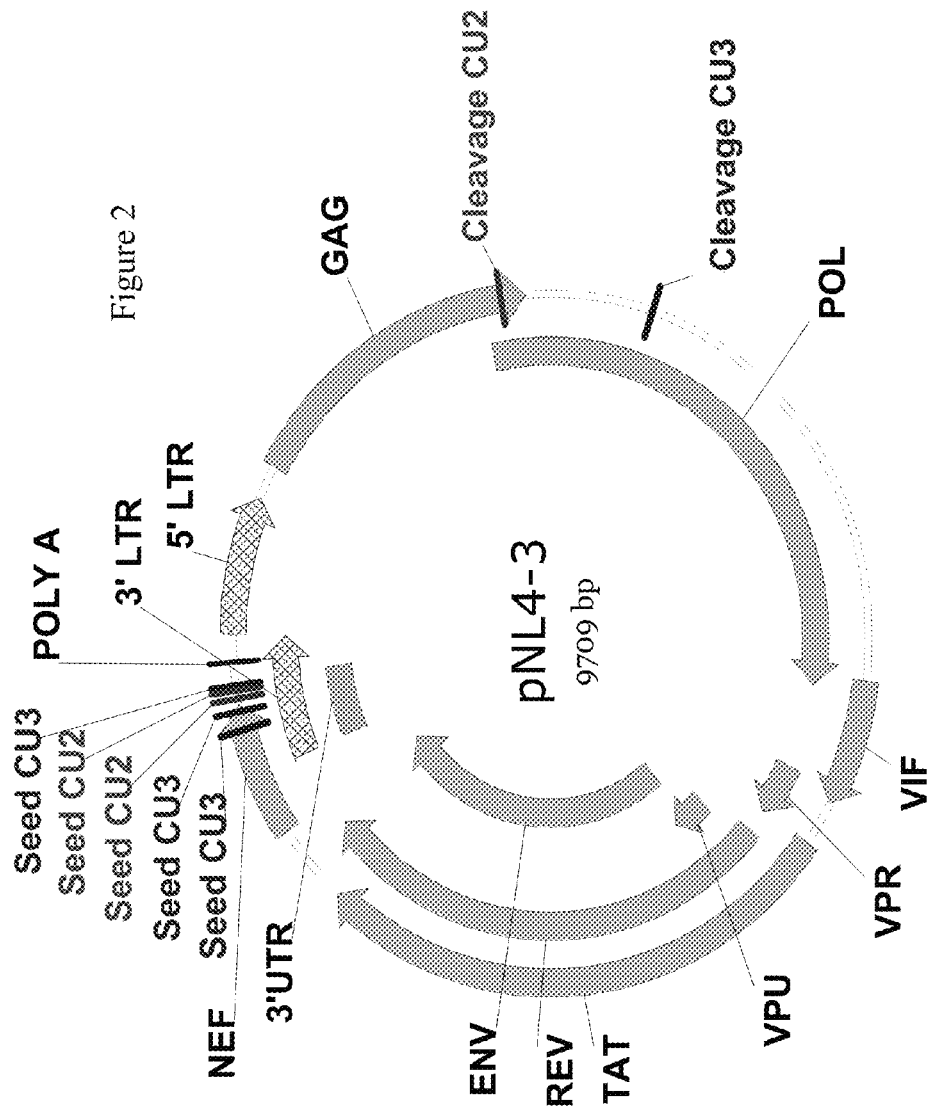
FIG. 2 shows target sites for multi-targeting siRNAs against HIV pNL4-3. This figure shows a schematic of the pNL4-3 genome (coding regions, 5' and 3' LTRs, and 3' UTR) and the position of the target sites for the two multi-targeting siRNAs we have designed to target pNL4-3. The siRNAs are called "CU2" and "CU3". CU2 has a cleavage site in GAG/POL and two seed sites in the 3' UTR; CU3 has a cleavage site in POL and three seed sites in the 3' UTR.
Figure 3:
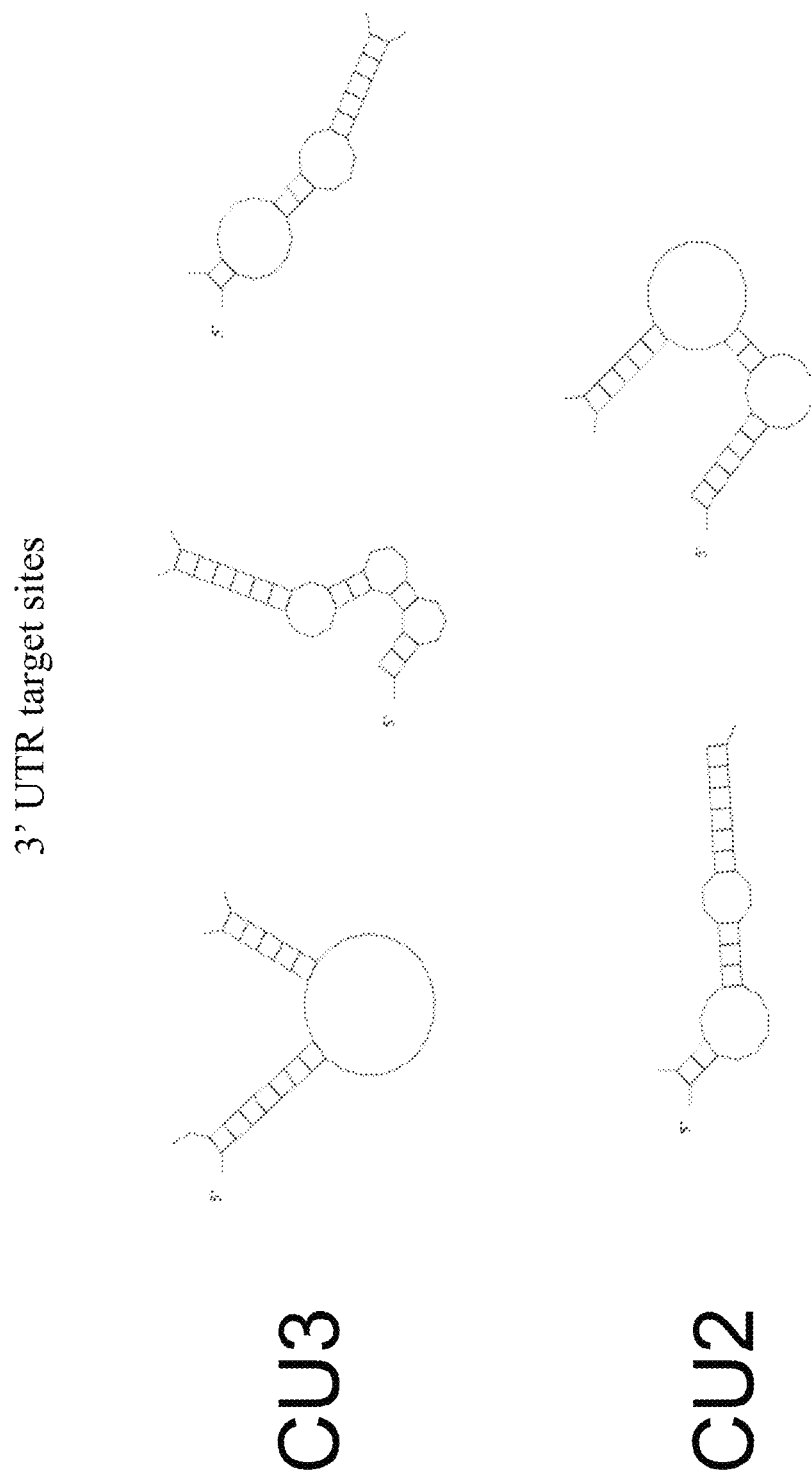
FIG. 3 shows a schematic of the base-pairing between the CU2 and CU3 siRNAs and their target sites in the pNL4-3 3' UTR.

The table lists the siRNA ID; the siRNA sense and antisense sequences; the location of the cleavage site within pol-gag; the location of the siRNAs' 3' UTR seed sites; and the distance between the seed sites.
These sites are shown schematically in FIG. 2 and the 3' UTR target cites are shown in FIG. 3.

TABLE 2 siRNAs Designed Against CCR5 mRNA and pNL4-3 3' UTR

| ID | sense/antisense (SEQ ID NO:/SEQ ID NO:) 5'-'3/3'-5' | CCR5 site | 3' UTR sites | Dist | Dist with CU3 | Dist with CU2 |
|---|---|---|---|---|---|---|
| CCR5_1 | gagaggagucagagagaau/ auucucucugacuccucuc (9/10) | 1034 (3' UTR) | 187, 242 | 55 | 32, 23, 61, 119 | 55, 120, 36 |
| CCR5_2 | aguccaaucuaugacauca/ ugaugucauagauuggacu (11/12) | 18 (CDS) | 330 | | 84, 27, 92 | 32, 36 |
| CCR5_3 | ucgguuugcagagcuuga/ ucaagcucugcaaaccaga (13/14) | 1160 (3' UTR) | 198, 338 | 140 | 21, 84, 35, 84 | 140, 24, 36 |
| CCR5_4 | ggugucgaaaugagaagaa/ uucuucucauuucgacacc (15/16) | 667 (CDS) | 24, 170 | 146 | 146, 49, 84, 119 | 146, 192, 36 |

Figure 4:
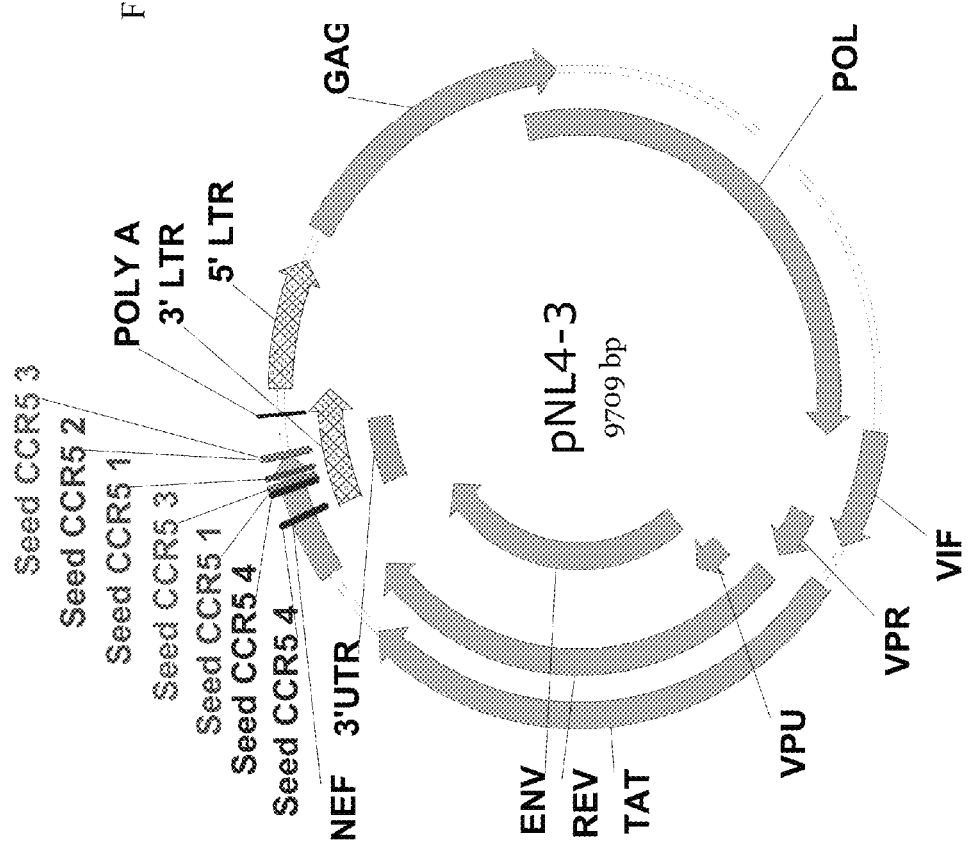
FIG. 4 shows seed sites for multi-targeting siRNAs against CCR5 and HIV pNL4-3. We have four siRNAs that have cleavage sites in CCR5 and seed sites in the pNL4-3 3' UTR. The position of the seed-sites are illustrated in this figure.
Figure 5:
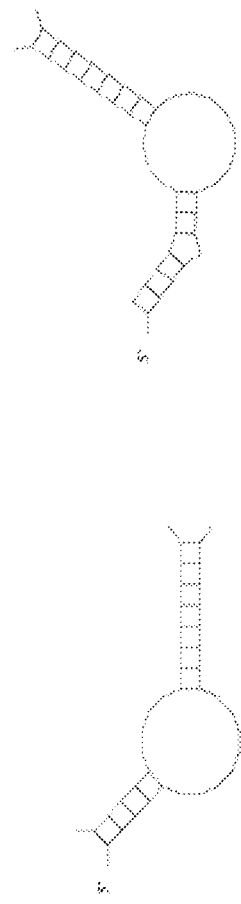
FIG. 5 shows a schematic of the base-pairing between two of the four siRNAs and their target sites in the pNL4-3 3' UTR.
Figure 6:
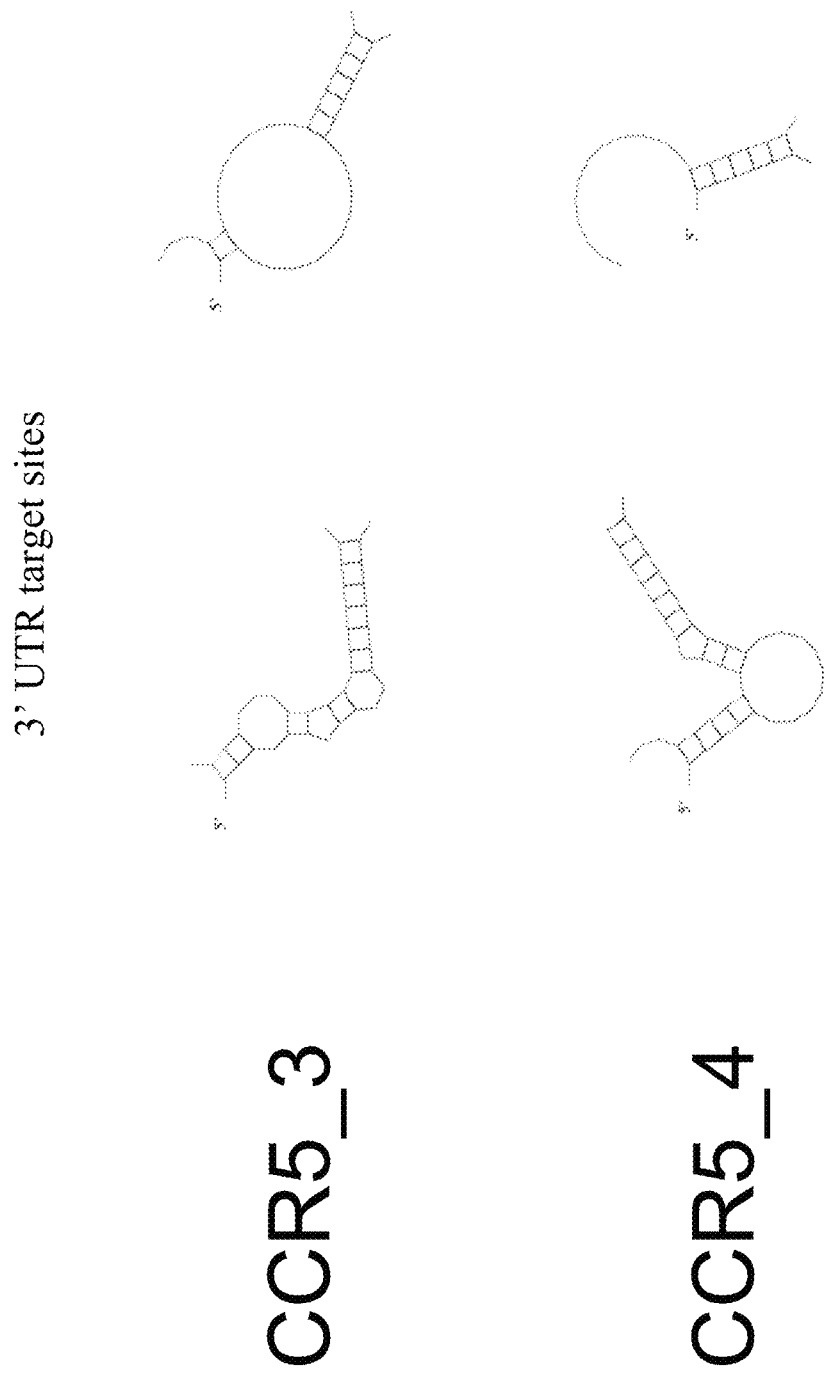
FIG. 6 shows a schematic of the base-pairing between two of the four siRNAs and their target sites in the pNL4-3 3' UTR.
Figure 7:
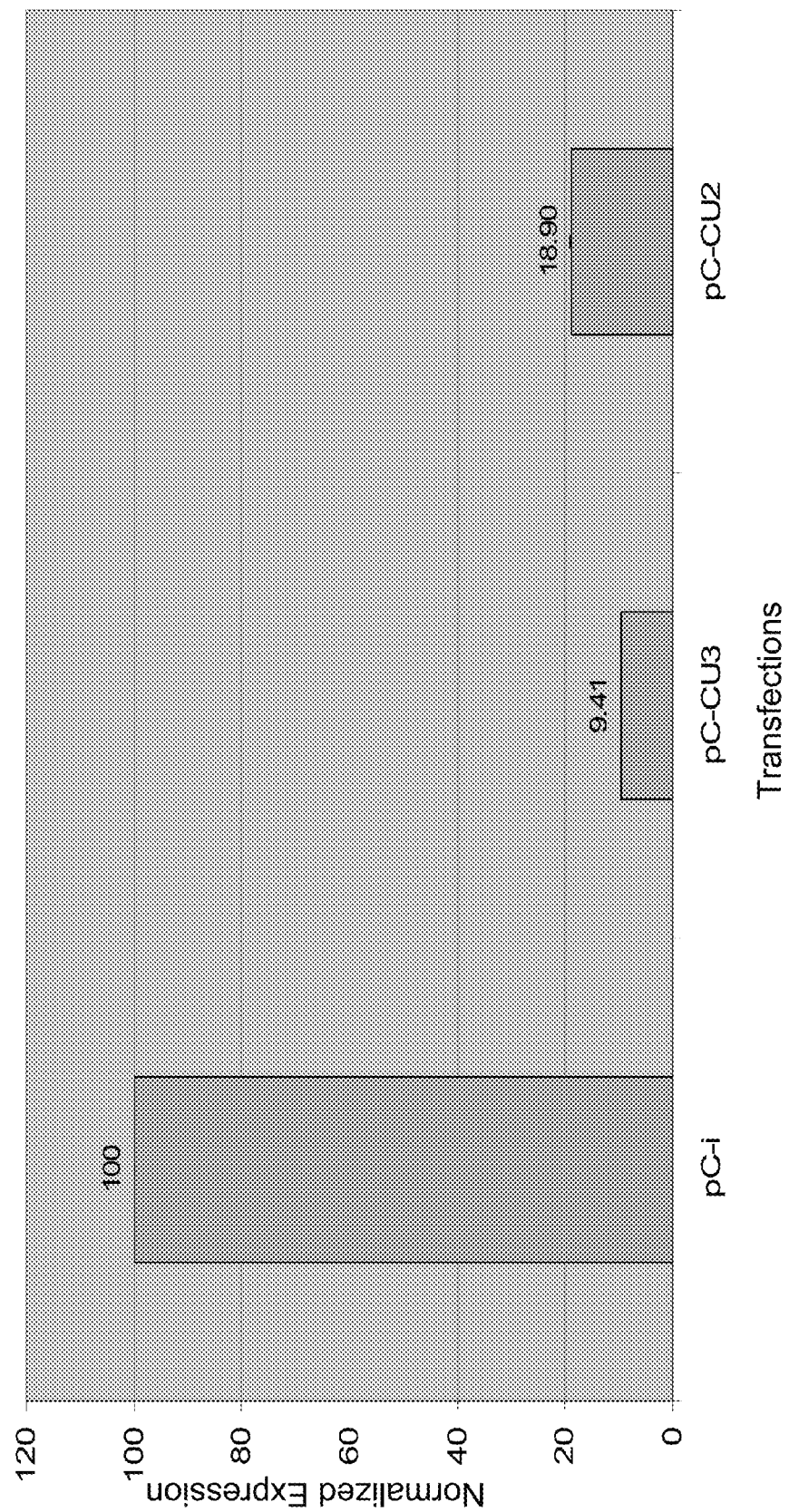
FIG. 7 shows the effect of siRNAs on coding sequences of pNL4-3.
Figure 8:
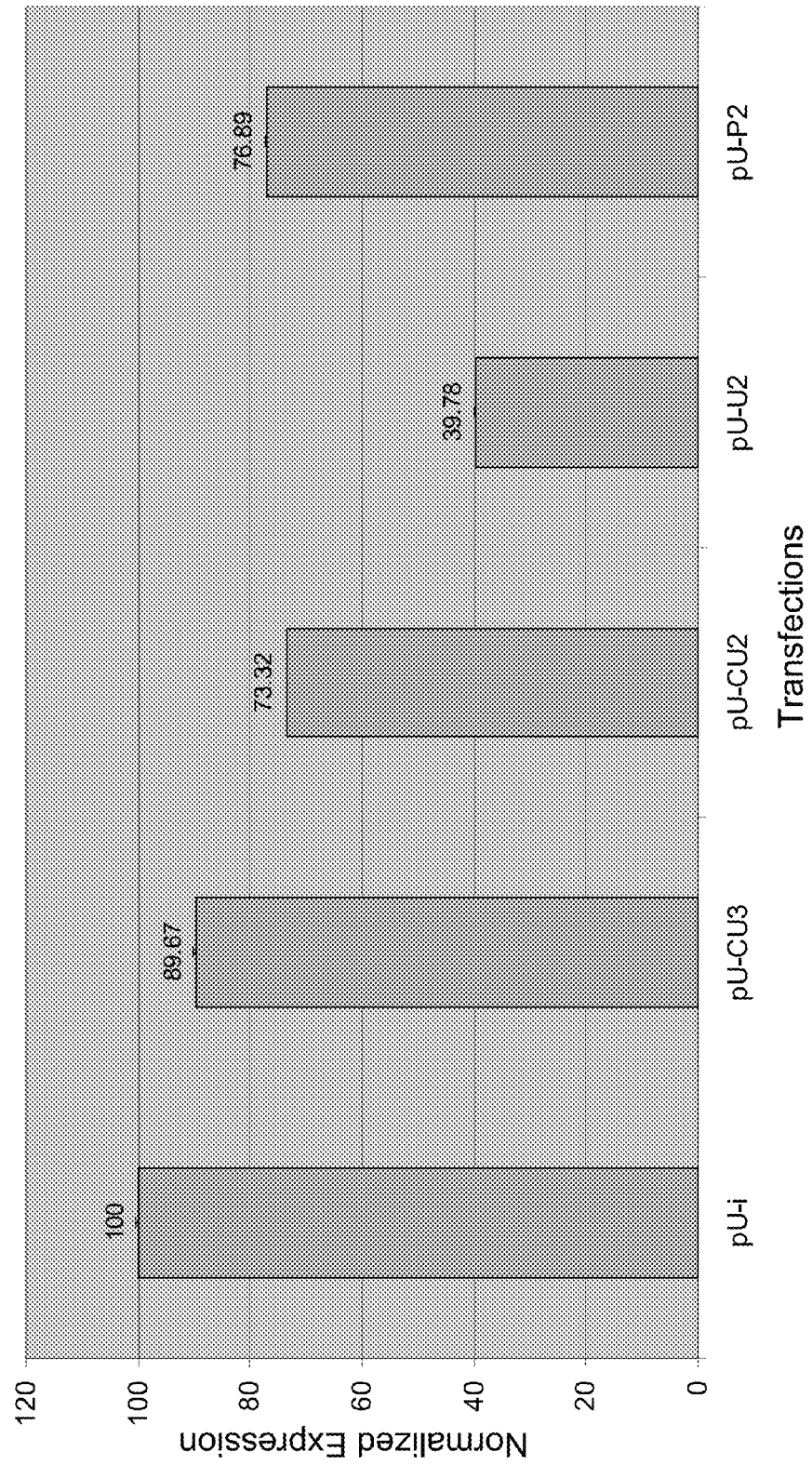
FIG. 8 shows the effect of miRNAs on 3' UTRs of pNL4-3.
Figure 9:
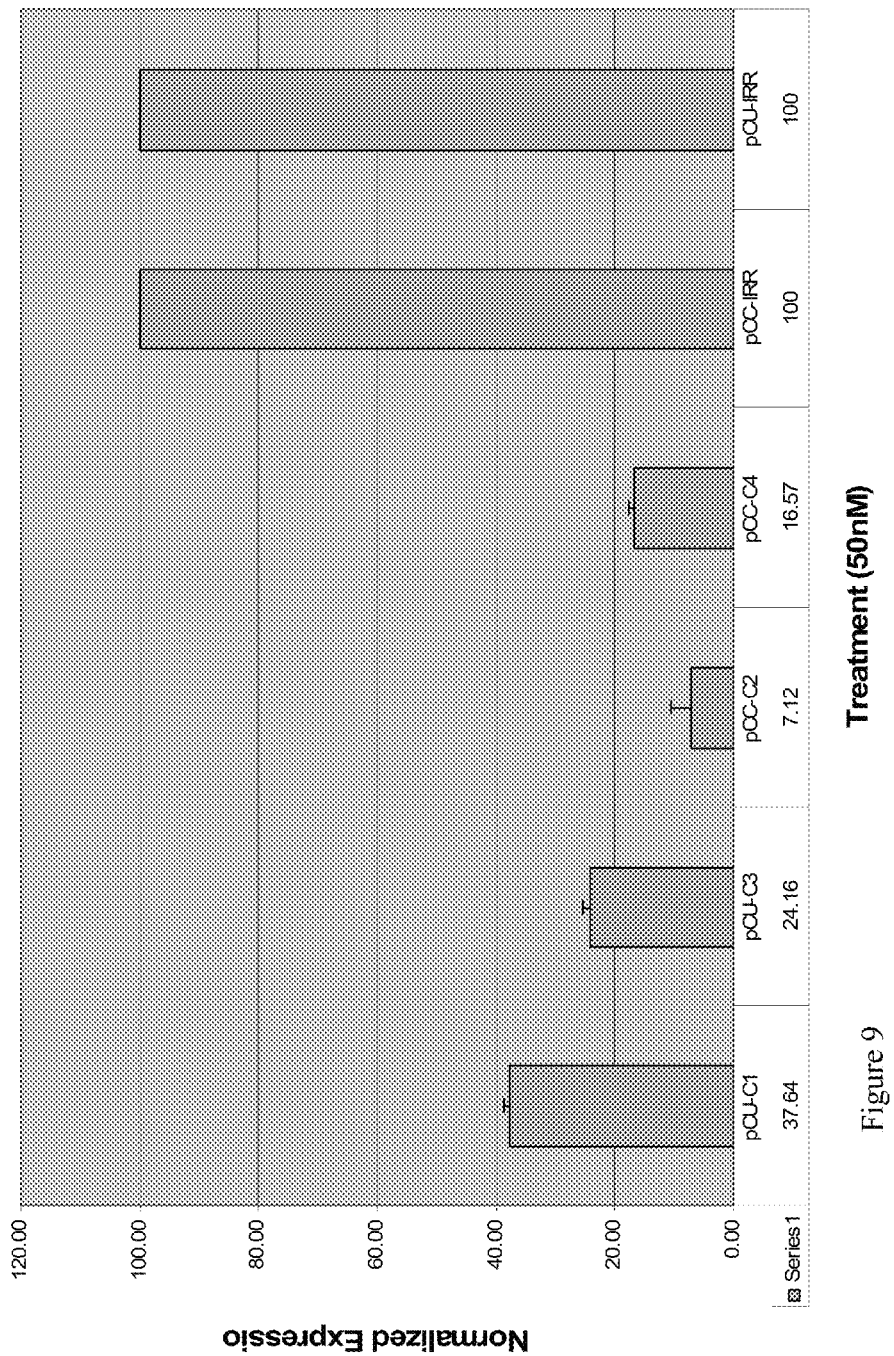
FIG. 9 shows the effect of siRNAs (C1-C4) on the CCR5 3'UTR and coding sequence regions.
Figure 10:
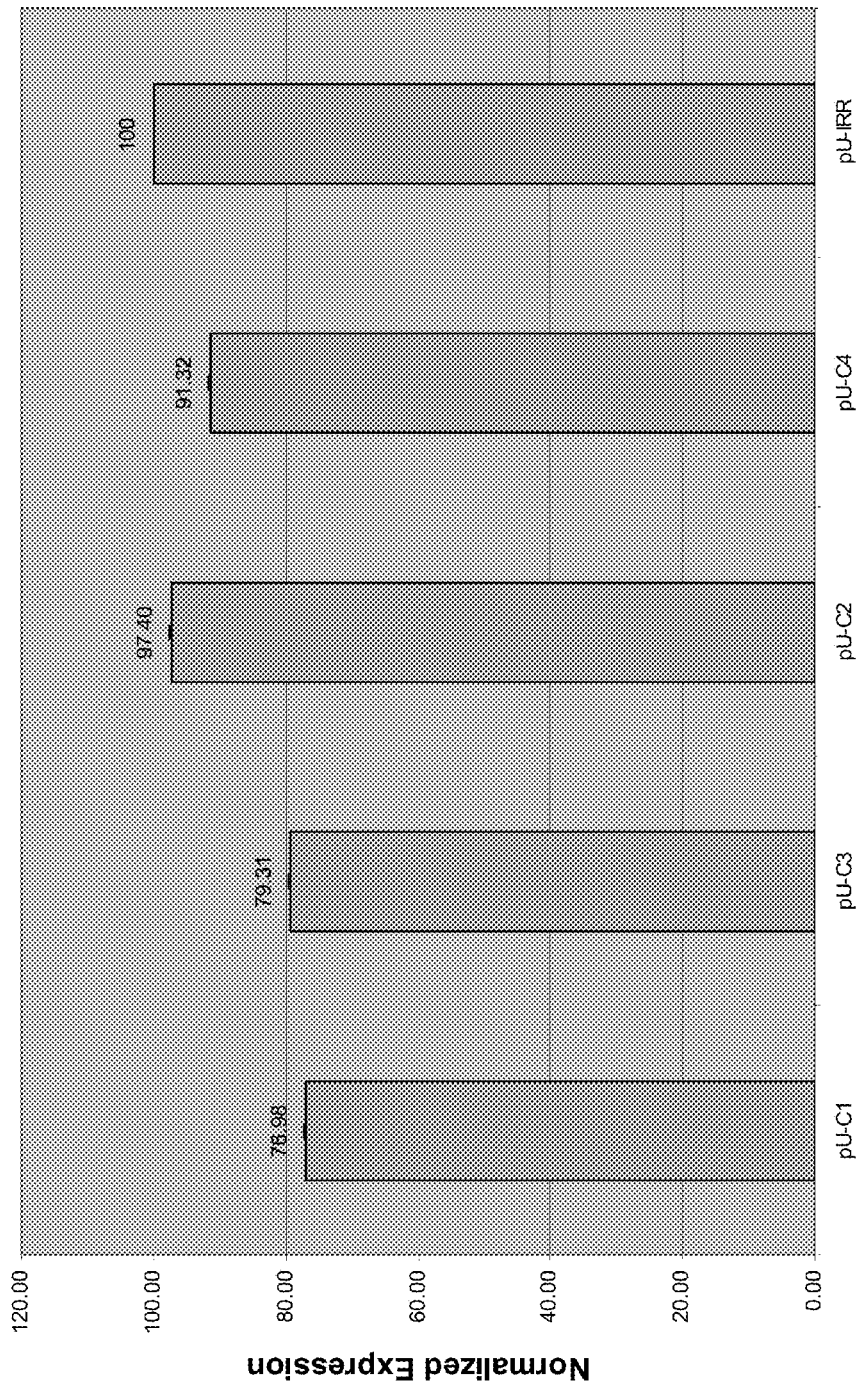
FIG. 10 shows the effect of various miRNAs on the pNL4-3 3' UTR region.
Figure 11:
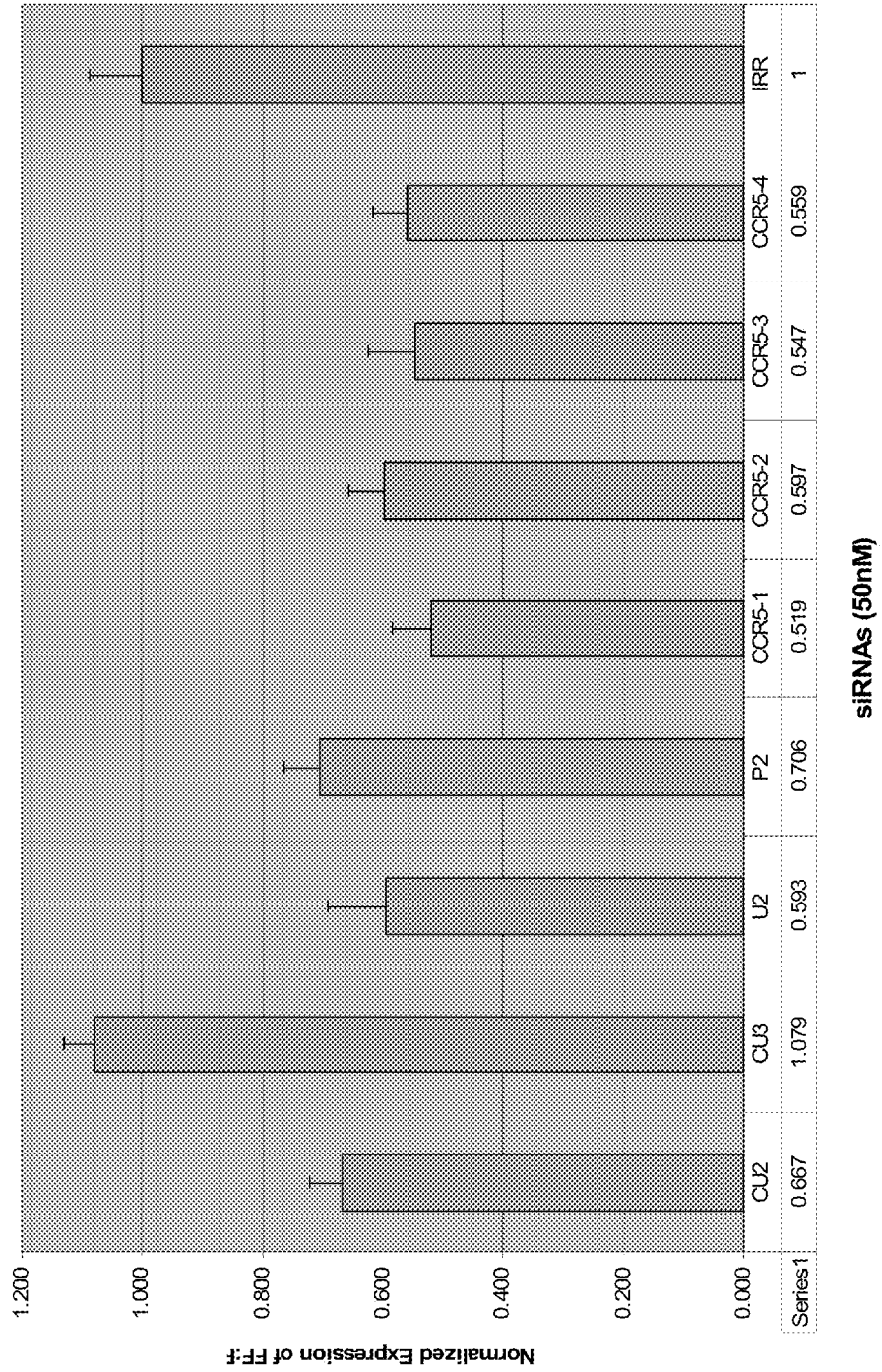
FIG. 11 shows the effect of various siRNAs on the pNL4-3 Luc reporter expression.

The table lists the siRNA ID; the siRNA sense and antisense sequences; the location of the cleavage site within CCR5; the location of the siRNAs' 3' UTR seed sites; and the distance between the seed sites; and the distances between the siRNA's and the seed sites for siRNAs CU3 and CU2.
These sites are shown schematically in FIG. 4 and the 3' UTR target cites are shown in FIGS. 5 and 6.

Example 2

Multi-Targeting siRNAs

Other multi-targeting siRNAs have been developed to several combinations of siRNA/miRNA targets for pNL4-3. These multi-targeting siRNAs are shown in Table 3.

TABLE 3

Multi-targeting siRNAs Designed Against Target Coding Sequences and 3' UTR in NL4-3

| CDS | siRNA (sense) (SEQ ID NO:) | 3' UTR sites | Dist |
|---|---|---|---|
| env seq | aagaguggugcagagagaa (17) | 187, 240, 242 | 53 |
| gag-pol seq | ucaggaaguauacugcauu (18) | 219, 303, 422 | 84, 119 |
| gag seq | gagcuucagguuuggggaa (19) | 362, 398 | 36 |
| Rev seq | gcccgaaggaauagaagaa (20) | 24, 170 | 144 |
| Vif seq | acauauugggguucugcaua (21) | 219, 303, 422 | 84, 119 |
| vpr seq | ggaacaagccccagaagac (22) | 24, 170 | 144 |

The table lists coding sequences in pNL4-3 (M19921) that are targeted by at least one multi-targeting siRNA.
The sequences for tat and vpu did not have any potential siRNA/miRNA combinations.
The table gives an example of the siRNA; the location of
the siRNAs 3' UTR seed sites; and the distance between the seed sites.

Each of the sequences listed in Table 3 are tested using chemically synthesized siRNAs and co-transfection assays of the siRNAs with pNL4-3 viral DNA. The ability of the siRNA to function is tested in co-transfections with pNL4-3 proviral DNA in 293 cells. Whether or not the siRNAs are also functioning as miRNAs it tested by cloning the NL4-3 3' UTR into a psiCHECK vector (Snove and Rossi, 2006) and monitoring the knockdown of luciferase expression in co-transfection assays.

Example 3

Multi-Targeting siRNAs to Two Targets

A hallmark of many types of B-cell lymphomas is the constitutive expression of oncogenes such as the transcription factors Bc1-6, STAT3 and c-Myc and the anti-apoptotic protein Bc1-2. Over expression of these genes causes uncontrolled proliferation and survival of malignant cells, making knockdown of these genes by RNA interference (RNAi) a rationale strategy for therapeutic intervention. RNAi is a conserved endogenous mechanism in which small interfering RNAs (siRNAs) suppress target-specific gene expression by promoting mRNA degradation. To target two of the critical B-cell lymphoma oncogenes, Bcl6 and STAT3, at the same time, we have designed bifunctional siRNA duplexes using different computer algorithms to predict accessible target sites in the mRNAs of the targets (Hossbach et al., 2006; http colon slash slash www dot mpibpc dot mpg dot de slash groups slash luehrmann slash siRNA). These bifunctional siRNAs contain two fully target-complimentary antisense strands against Bcl6 and STAT3 mRNAs, respectively, but that are only partially complementary to each other. Bifunctional siRNAs have the advantage to provide two antisense strands simultaneously suggesting the reduction of effective concentration transfected to the cells. Additionally, bifunctional siRNAs might also show increased specificity and decreased off-target effects compared to conventional 21mers due to the lack of undesired activity of the passenger strand.

Different designs of the bifunctional siRNAs are possible: a) 21mer with 2 nt 3' overhang at both strands (conventional siRNA design), b) 27mer Dicer-substrate with single 2 nt 3' overhang and 3' DNA residues at the blunt end (asymmetrical design), c) 27mer with 2 nt 3' overhang at both strands, d) 27mer with blunt ends at both strand. All siRNAs were chemically synthesized. The structures of the bifunctional siRNAs are set forth below. Numbers indicate the target site in the mRNA sequences of Bcl6 and STAT3, respectively. RNA bases are upper case, DNA bases are lower case. In vitro cleavage assays indicate that our bifunctional siRNAs have sufficient complementarity to form stable duplexes and can be processed into smaller molecules by recombinant Dicer.

BS-1100 (Bcl6 1100, STAT3 3822)

a) 21 mer design

5'    UAGACACGCAAGGAGACAUGC   3' (SEQ ID NO: 23)
      ||  |||  ||||||•|||
3' AGAUAAGUGGGUUCCUUUGUU      5' (SEQ ID NO: 24)

b) 27mer design (asym.)

5'    UAGACACGCAAGGAGACAUGCCag  3' (SEQ ID NO: 25)
      ||  |||  ||||||•|||  ||||||
3' AGAUAAGUGGGUUCCUUUGUUCGGGUC  5' (SEQ ID NO: 26)

c) 27mer (3' overhang)

5'    UAGACACGCAAGGAGACAUGCCUCAG 3' (SEQ ID NO: 27)
      ||  |||  ||||||•|||  |||:
3' AGAUAAGUGGGUUCCUUUGUUAGGGUC   5' (SEQ ID NO: 28)

d) 27 mer design (blunt)

5' UUUAGACACGCAAGGAGACAUGCCUCU   3' (SEQ ID NO: 29)
   |:||   |||  ||||||•|||   |||:
3' AGAUAAGUGGGUUCCUUUGUUAGGGUC   5' (SEQ ID NO: 30)

BS-2755 (Bcl6 2755, STAT3 4576)

a) 21 mer design

5'    GCAGACUAAAGUCAAG UCAUG   3' (SEQ ID NO: 31)
      ||||          ||||||  |||
3' CUCGUCUAUAA CAGUUCAAGU    5' (SEQ ID NO: 32)

b) 27mer design (asym.)

5'    GCAGACUAAAGUCAAG UCAUGGCct 3' (SEQ ID NO: 33)
      ||||          ||||||  ||||||||||
3' CUCGUCUAUAA CAGUUCAAGUACCGGA   5' (SEQ ID NO: 34)

c) 27mer (3' overhang)

5'    GCAGACUAAAGUCAAG UCAGAACUUUU 3' (SEQ ID NO: 35)
      ||||          ||||||  |||   |:|
3' CUCGUCUAUAA CAGUUCAAGUACCGGA     5' (SEQ ID NO: 36)

d) 27mer (Blunt)

5' UUGCAGACUAAAGUCAAG UCAGAACUU  3' (SEQ ID NO: 37)
   ||||          ||||||  |||   |:|
3' CUCGUCUAUAA CAGUUCAAGUACCGGA  5' (SEQ ID NO: 38)

BS_1248 (Bcl6 1248, STAT3 1028)

b) 27 mer design (asym.)

5'    GGGCA   AUCUCAUCUUCCGACCCGtc  3' (SEQ ID NO: 39)
      ||||    ||||||  ||||  |||||||||
3' AUCGUCUUAGAGUUGAAGUCAGGGCAG      5' (SEQ ID NO: 40)

Figure 12:
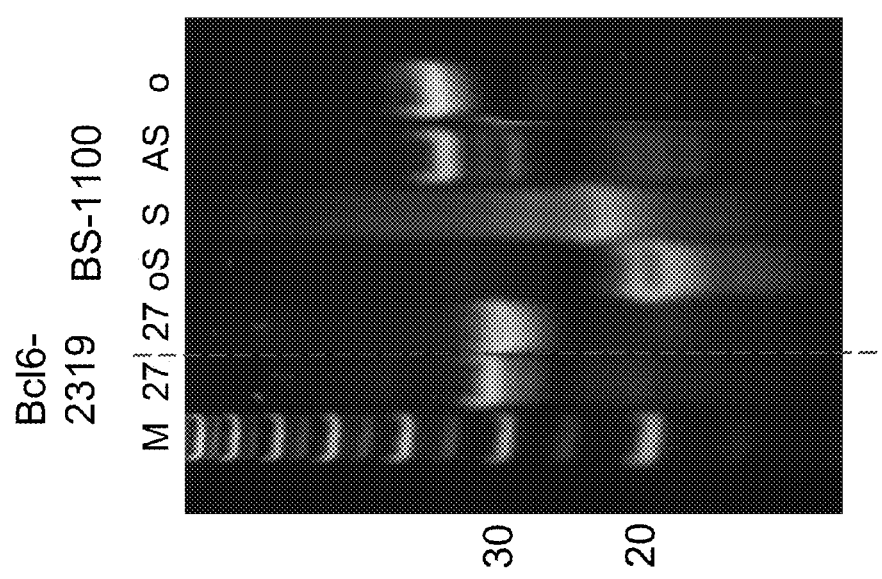
FIG. 12 shows the analysis of bifunctional siRNA duplexes against Bcl6 and STAT3 at the same time on a 15% native gel that was stained with SYBR Gold. Legend: 27=asymmetrical design, o=overhang, b=blunt, S=sense strand only, AS=antisense strand only.

To determine duplex formation and stability of bifunctional siRNAs targeting Bcl6 and STATS, the sense and antisense strand of different designs were denatured at 80° C. and then slowly cooled down to room temperature. The duplexes were analysed on a 15% native gel and stained with Sybr Gold (FIG. 12). A full complementary conventional siRNA against Bcl6 was used as reference (lane: Bcl6). All bifunctional siRNAs form duplexes, but most of the analyzed solutions contain single strands besides the duplex. Exceptions are BS-1100-27 and BS-1100-o that seem to form only stable duplexes.

Figure 13:
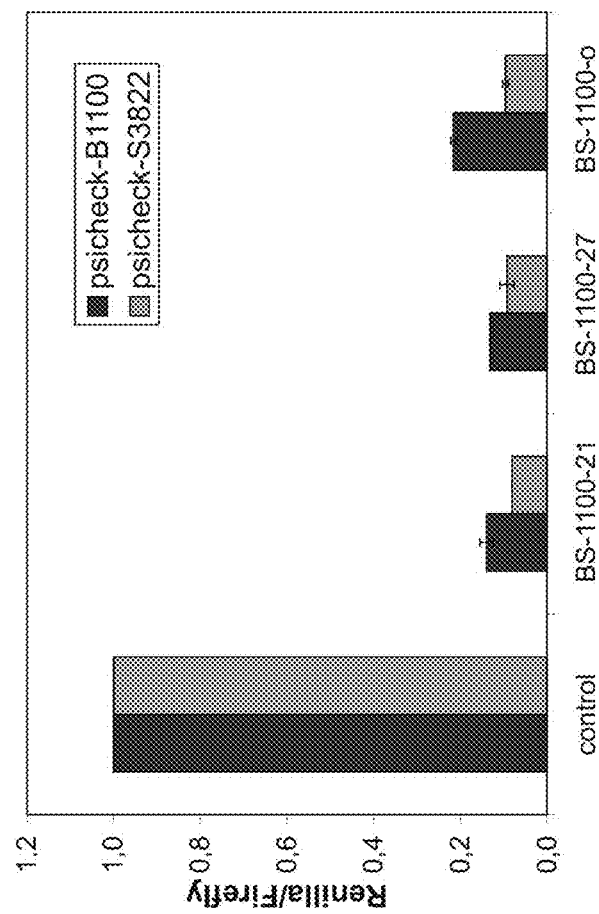
FIG. 13 shows the results of the psicheck assay for different designs of multi-targeting siRNAs for BS-1100.

Silencing efficacy was determined by psicheck assay (FIG. 13). Target sites of the different siRNAs were cloned in the psicheck vector and cotransfected with corresponded bifunctional siRNA in HEK293 cells. Renilla and firefly luciferase activity was measured 24 h after transfection and values were normalized to the control. FIG. 13 shows clearly that the bifunctional siRNA BS-1100 is working against both targets.

Figure 14:
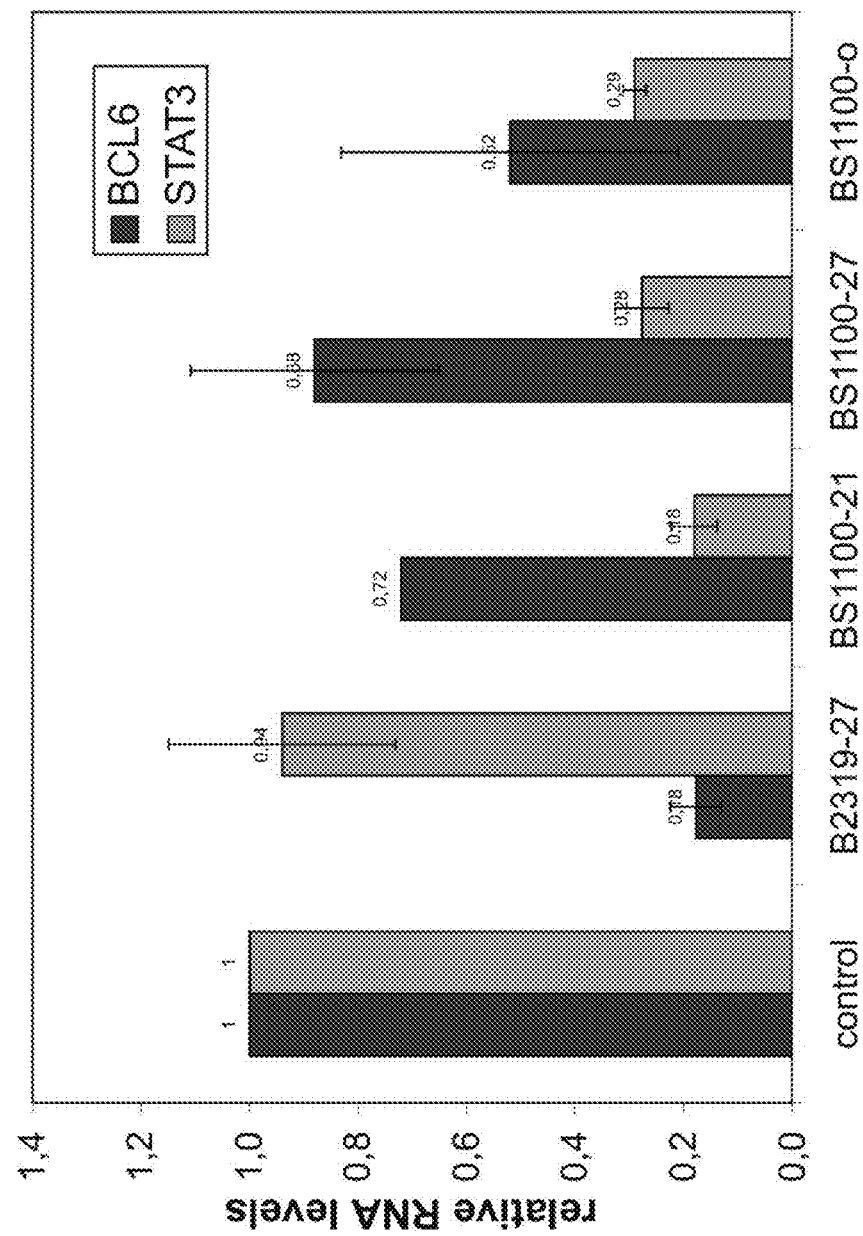
FIG. 14 shows real-time PCR performed for STAT3 and Bcl6 mRNAs extracted from HEK293 cells 48 h after transfection of 50 nM siRNAs with RNAiMax. The first number after the target molecule name represents the target site in the mRNA sequence, the second number indicates asymmetrical Dicer substrate (27mer) or the 21mer siRNA. STAT3 and BCL6 mRNA levels were normalized to RPLP0 and are shown relative to the mock transfected control. Experiments were done in triplicate.

To determine the efficacy of the bifunctional siRNAs, conventional 21mers and asymmetrical 27mers were transfected into HEK293 cells using cationic lipids (RNAiMax, Invitrogen) and total RNA was collected 48 h post-transfection for quantitative RT-PCR. Target gene expression was normalized to levels of RPLP0 mRNA, a ribosomal protein that is an established reference gene. All analyzed bifunctional siRNAs were able to reduce STAT3 mRNA levels by 50 to 80% as determined by quantitative RT-PCR (FIG. 14).

Figure 15:
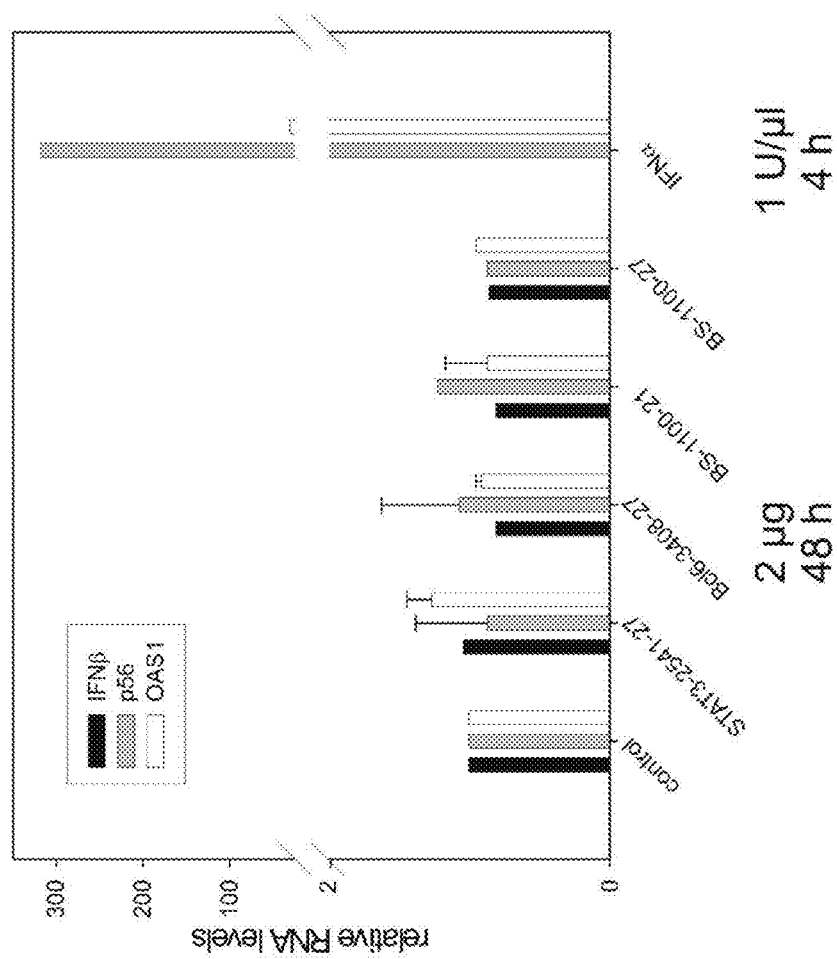
FIG. 15 shows real-time PCR performed for IFNβ, p56 and OAS1 mRNAs extracted from Raji cells 48 h after electroporation of 2 µg siRNA following the Amaxa protocol. As positive control, Raji cells were incubated with 1 U/µl IFNα for 4 h. Data was normalized to RPLP0 and is shown relative to the mock transfected control. Experiments were done in duplicate.

The effect of the bifunctional siRNAs on interferon pathway related genes in different cell types was analyzed using real-time PCR. The real-time PCR was performed for IFNβ, p56 and OAS1 mRNAs extracted from Raji cells 48 h after electroporation of 2 μg siRNA following the Amaxa protocol. As positive control, Raji cells were incubated with 1 U/μl IFNα for 4 h. Data was normalized to RPLP0 and is shown in FIG. 15 relative to the mock transfected control. Experiments were done in duplicate. Similar results were obtained for Daudi, Su-DHL-4 and Su-DHL-6 cell lines. The results demonstrate that none of the analyzed siRNAs show a significant increase in the expression of interferon pathway related genes in different cell lines.

In these experiments, we found that the most effective siRNAs reduce target mRNA levels by ~80% as determined by quantitative RT-PCR and immunoblot analysis. The bifunctional siRNAs are able to silence effectively two critical B-cell lymphoma oncogenes at the same time. In addition, we found that the silencing of Bcl6 affects the expression of downstream target genes. Finally, we found that none of the analyzed siRNAs show a significant increase in the expression of interferon pathway related genes in different cell lines.

Example 4

Targeting Two Genes on Separate Strands of siRNA

Figure 16A:
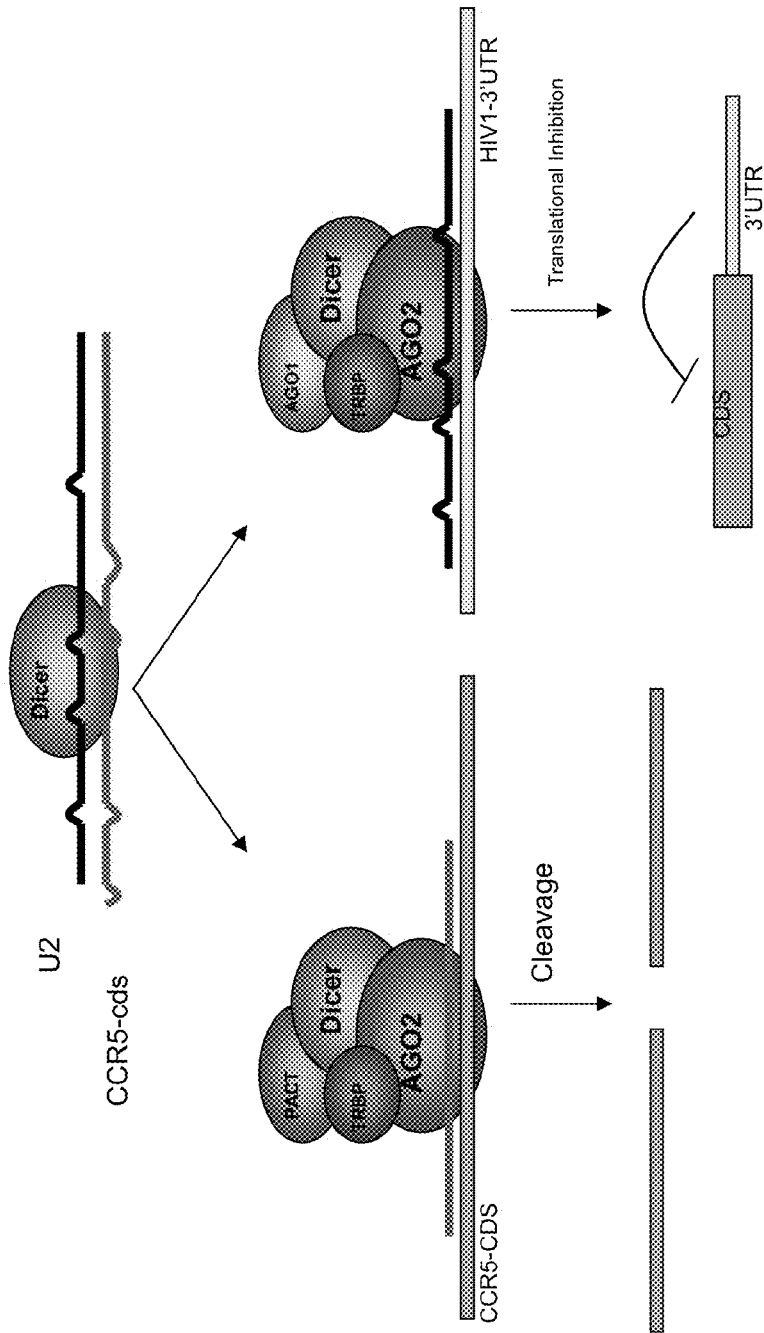
FIGS. 16A and 16B show a proposed model for incorporation and processing of the Dicer-substrate multi-functional siRNAs.
Figure 16B:
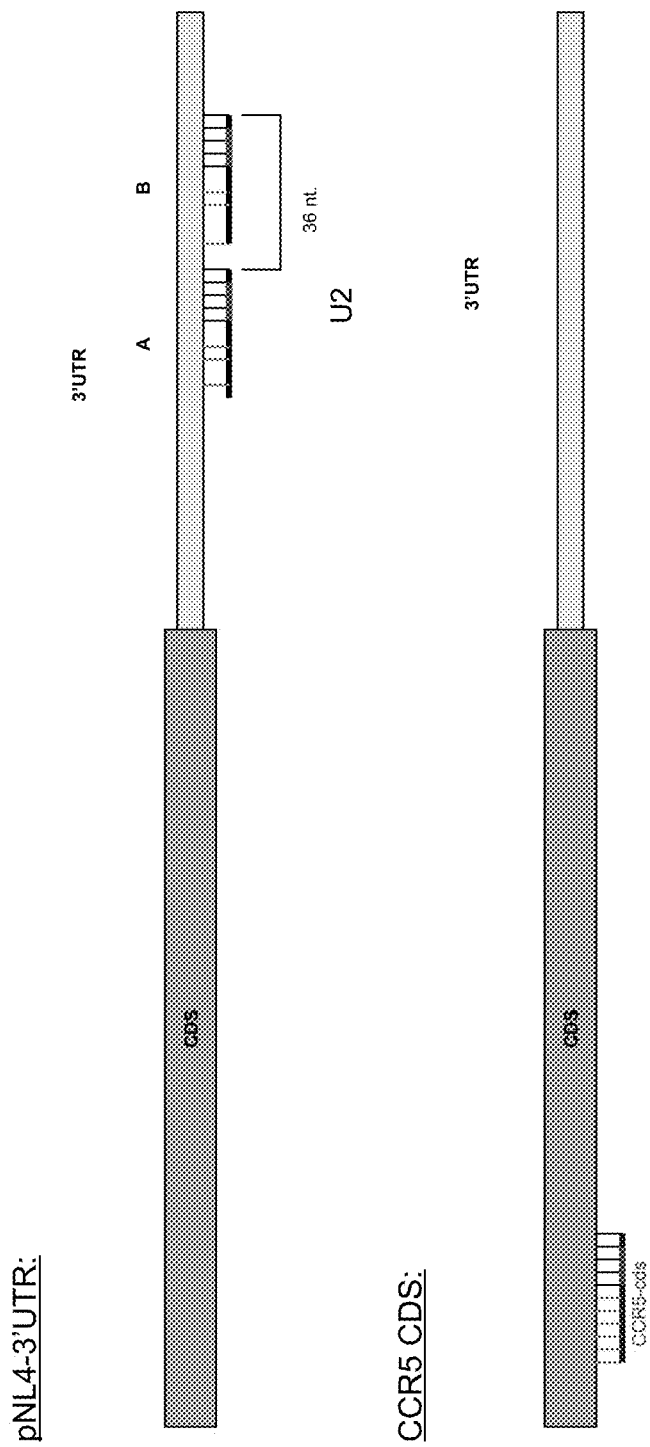
Figures 17A, 17B:
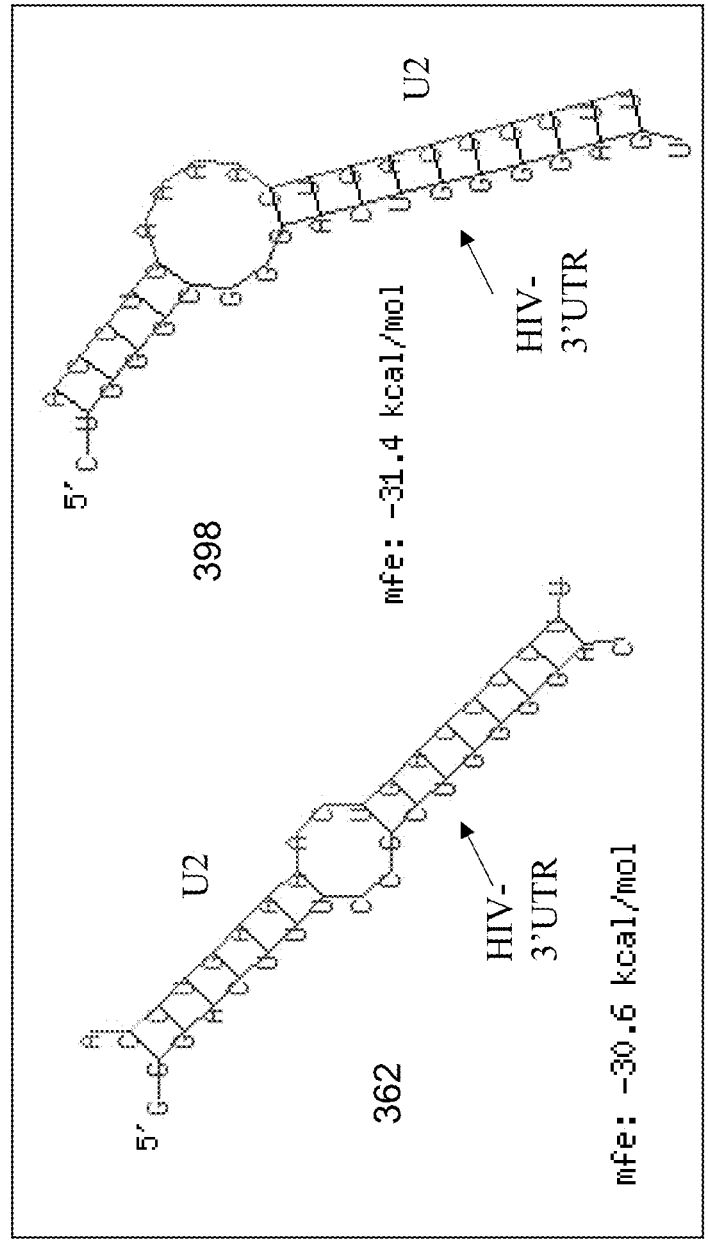
FIGS. 17A and 17B show the structures of U2 miRNA (left strands) bound to the two 3' UTR sites of HIV (right strands). The U2 miRNA upstream of the seed sequence has differential complementarity against the HIV 3' UTR sites.
Figures 19A, 19B:
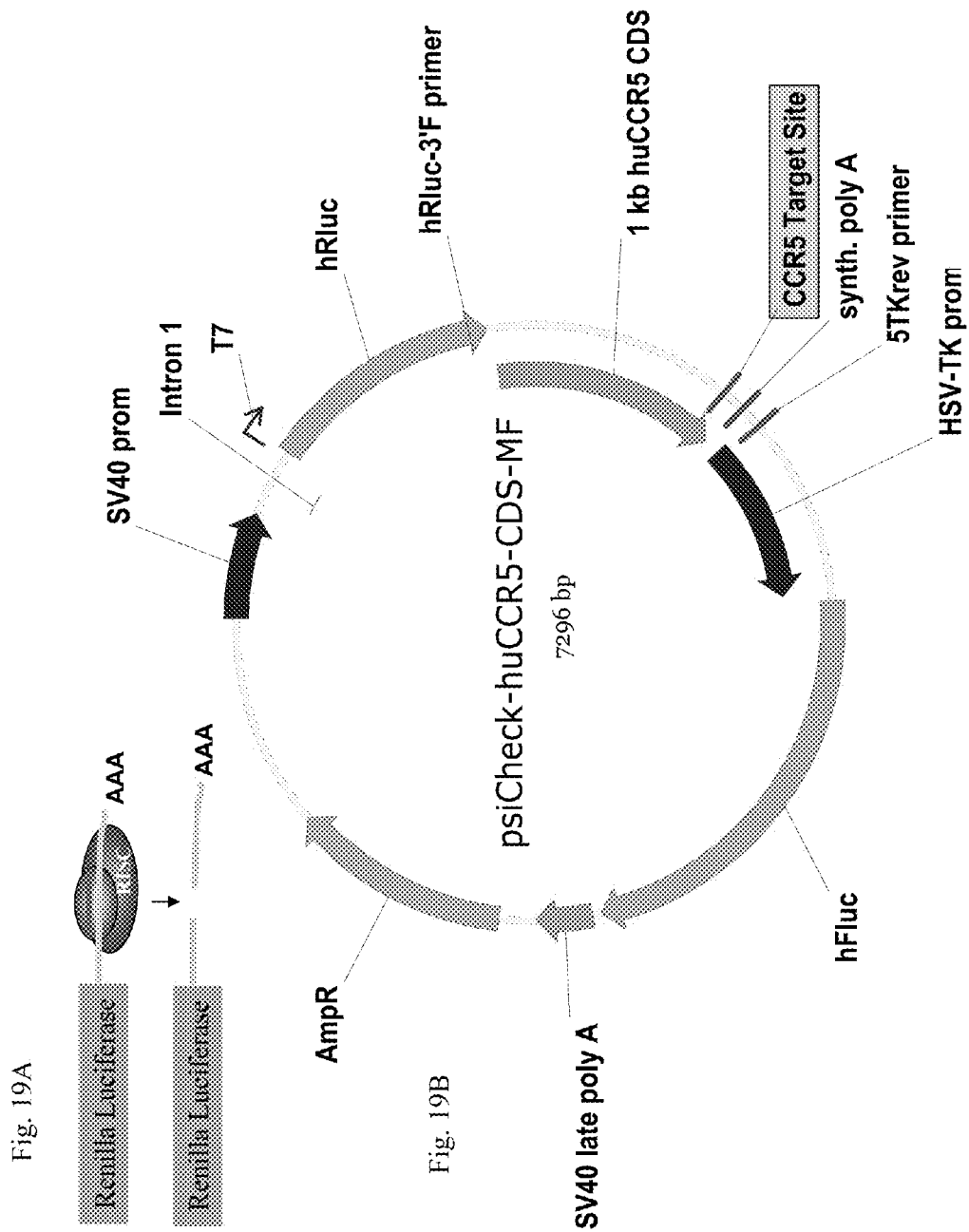
FIGS. 19A and 19B show a schematic of the reporter pCC.

Multi-functional siRNAs are designed so that each strand of the duplex targets a specific sequence. In this design both strands of the siRNA duplex are used as triggers and can incorporate into various RISC complexes (FIG. 16A). The two strands of the designed siRNA duplex can target one mRNA at the 3'UTR and another mRNA at the coding region. Using HIV as an example, multi-strand siRNAs are designed so that one strand targets the HIV 3'UTR and the other strand targets the HIV or the CCR5 coding region simultaneously. In our design the top strand, which is the U2 anti-sense strand, functions as an miRNA against the HIV 3'UTR and the bottom strand, which has perfect complementarity against either the CCR5 or the HIV coding region (Tables 4 and 5), functions as an siRNA (FIG. 16B).

The predicted structures of the multi-functional siRNAs shown in Table 5 are as follow.

```
U2-CCR5-3p:
(top: SEQ ID NO: 45; bottom: SEQ ID NO: 46):
top     5'   U    C   AA      CCA          3'
             UCCC AGUC   AAGU    AUUGGA
             AGGG UCAG   UUCG    UAACCU
bottom  3'   CUU    A    AAG   UC           5'

U2-CCR5-cds:
(top: SEQ ID NO: 47; bottom: SEQ ID NO: 48)
top     5'        C    U   A      A          3'
             UUC CCAG CAA AG   UCC CGAGCG
             AAG GGUC GUU UC   AGG GCUCGC
bottom  3'   AU    A        C   CG           5'

U2-PolGag-cds:
(top: SEQ ID NO: 49; bottom: SEQ ID NO : 50)
top     5'        UCAAA   CCA               3'
             UUCC CCAG   AGU    AGGUUU
             GGGG GGUC   UCG    UCCAAA
bottom  3'   UC    U     UUCUC   AAG         5'

U2-HIV1-3p:
(top: SEQ ID NO: 51; bottom: SEQ ID NO: 52)
top     5'        C      AAA    CA          3'
             CCA  GUCA   GUC   AUAUCC
             GGU  CGGU   CAG   UAUAGG
bottom  3'   UGUGU  CC      CCC   UC         5'
```

The predicted target site interactions for CCR5_5 are as follows.

```
position 385:
     (target: SEQ ID NO: 53; miRNA: SEQ ID NO: 54)
```

TABLE 4

Sequences of the Bottom Strand (siRNA strand) and Their Mismatches with the U2 Anti-sense Strand (miRNA Strand)

| ID | Reporter | Target site (sense) (SEQ ID NO) | Mismatches w/U2 |
|---|---|---|---|
| U2-CCR5-3p | CCR5 3' UTR | AUCCCUAGUCUUCAAGCAG (41) | 7 |
| U2-CCR5-cds | CCR5 CDS | UUUUCCAGCAAGAGGCUCCC (42) | 7 |
| U2-PolGag-cds | pNL4-3 PolGag CDS | CCCACCAGAAGAGAGCUUCA (43) | 9 |
| U2-HIV1-3p | HIV1 3' UTR | ACACCAGGGCCAGGGGUCAG (44) | 11 |

TABLE 5

Dicer Substrate Multi-strand siRNAs

| ID | top-25mer based on U2 (SEQ ID NO) | bottom-27mer cleavage strand (SEQ ID NO) |
|---|---|---|
| U2-CCR5-3p | uucccagucaaaaguccaAUUGGA (45) | uccaaucugcuugaagacuagggauuc (46) |
| U2-CCR5-cds | uucccagucaaaaguccaCGAGCG (47) | cgcucgggagccucuugcuggaagaua (48) |
| U2-PolGag-cds | uucccagucaaaaguccaAGGUUU (49) | aaaccugaagcucucuucuggugggcu (50) |
| U2-HIV1-3p | uucccagucaaaaguccaAUAUCC (51) | ggauaucugacccuggcccuggugugu (52) |

The top strand is the U2 anti-sense strand (lower case) extended with nucleotides 3' of the cleavage site (upper case).
The bottom strand is reverse-complementary to the cleavage site.

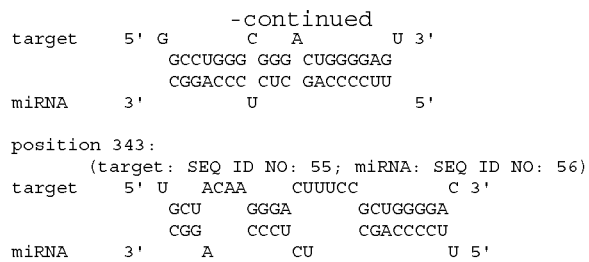

```
position 343:
    (target: SEQ ID NO: 55; miRNA: SEQ ID NO: 56)
target    5' U  ACAA      CUUUCC      C 3'
             GCU  GGGA        GCUGGGA
             CGG  CCCU        CGACCCU
miRNA     3'   A     CU           U 5'
```

Figure 20:
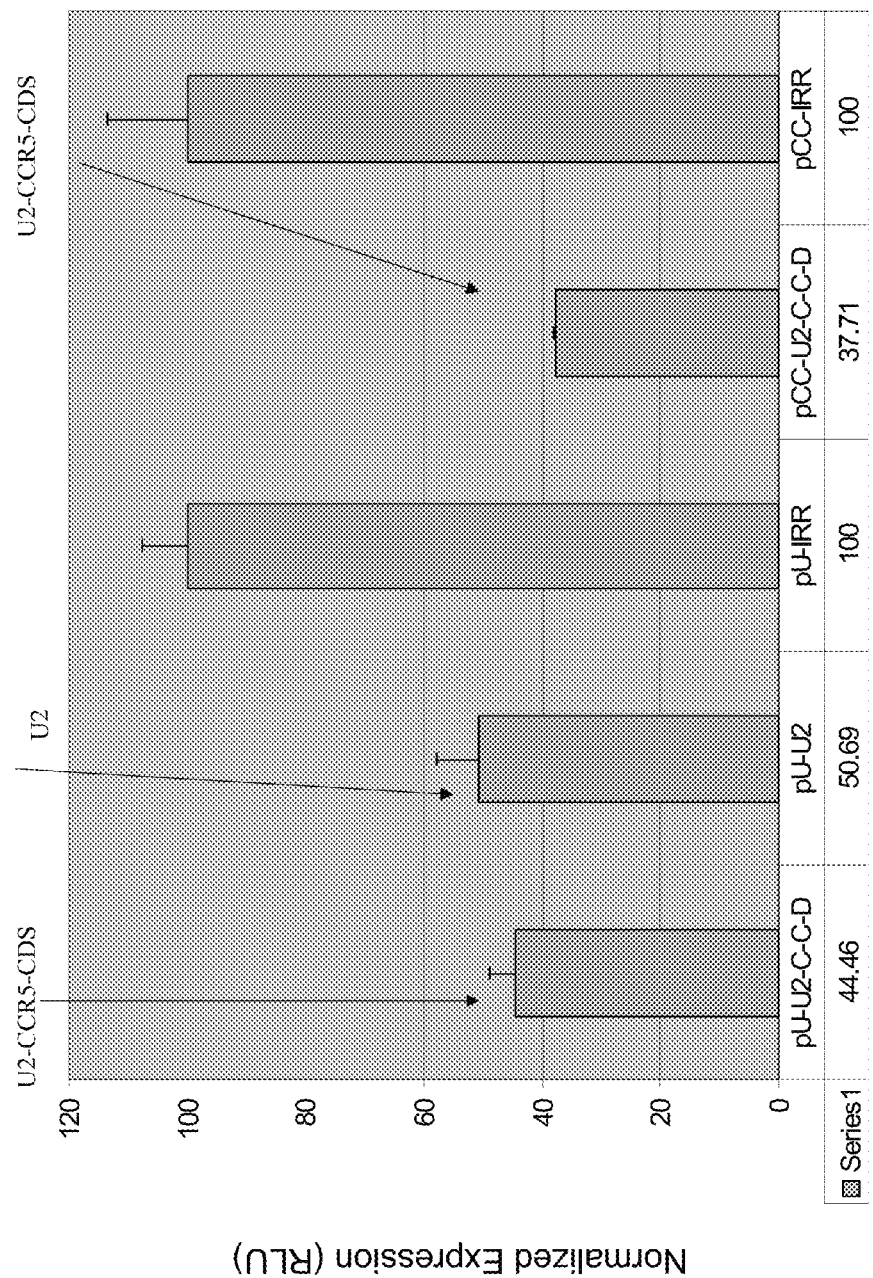
FIG. 20 shows the effect of the multi-functional siRNAs on the HIV-1 3'UTR and CCR5-CDS psiCheck Reporter Constructs. The synthetic Dicer-substrate U2-CCR5-cds multifunctional siRNA (U2-C-C-D) was cotransfected with the psiCheck reporter expressing the HIV 3' UTR (pU). Twenty four hours post transfection the cells were harvested, lysed and subjected to Luciferase assay. The expression of Renilla Luciferase gene was reduced to 44.46 percent relative to the control irrelevant (pU-IRR) siRNA cotransfected with the pU reporter as well as the perfectly matched U2 siRNA (top center of the chart) transfected with the pU reporter (pU-U2), 50.69 percent. The downregulation of the Renilla expression is indicating processing of the Dicer-substrate multifunctional siRNA and incorporation of the U2 miRNA strand into RISC. The efficiency and potency of the U2 miRNA in the context of the multifunctional Dicer-substrate duplex (left to right, first bar, 44.46%)) was even better compared to the conventional 21 mer perfect siRNA duplex of U2 (left to right, second bar, 50.69%). The incorporation of the bottom strand of the Dicer-substrate multifunctional siRNA was validated by cotransfecting the multi-functional siRNA with the reporter psiCheck construct containing one kilobase pairs of the CCR5 coding region (pCC, target). The expression of the Renilla Luciferase gene was reduced to 37.71 percent (pCC-U2-C-C-D) (Left to right forth bar) relative to the irrelevant control (pCC-IRR) (Left to right, last bar). The downregulation of the Renilla expression is indicating processing of the Dicer-substrate multifunctional siRNA and incorporation of the anti-CCR5 strand into RISC. All of the transfections were done in triplicates.

Results of these multi-functional siRNAs are shown in FIGS. 17-20. FIGS. 17A and 17B show the structures of U2 miRNA bound to the two 3' UTR sites of HIV. FIGS. 18A and 18B show a schematic of the reporter pU. FIGS. 19A and 19B show a schematic of the reporter pCC. As shown in FIG. 20, the expression of Renilla Luciferase gene was reduced to 44.46 percent relative to the control irrelevant (pU-IRR) siRNA cotransfected with the pU reporter as well as the perfectly matched U2 siRNA (top center of the chart) transfected with the pU reporter (pU-U2), 50.69 percent. The downregulation of the Renilla expression is indicating processing of the Dicer-substrate multifunctional siRNA and incorporation of the U2 miRNA strand into RISC. The efficiency and potency of the U2 miRNA in the context of the multifunctional Dicer-substrate duplex (left to right, first bar, 44.46%) was even better compared to the conventional 21 mer perfect siRNA duplex of U2 (left to right, second bar, 50.69%). The incorporation of the bottom strand of the Dicer-substrate multifunctional siRNA was validated by cotransfecting the multi-functional siRNA with the reporter psiCheck construct containing one kilobase pairs of the CCR5 coding region (pCC, target). The expression of the Renilla Luciferase gene was reduced to 37.71 percent (pCC-U2-C-C-D) (Left to right forth bar) relative to the irrelevant control (pCC-IRR) (Left to right, last bar). The downregulation of the Renilla expression is indicating processing of the Dicer-substrate multifunctional siRNA and incorporation of the anti-CCR5 strand into RISC.

All together, the data shows that multifunctional siRNA designs made up of two functional strands are recognized by the intracellular protein machineries responsible for RNAi phenomena. These novel siRNAs are processed efficiently by the Dicer protein complex and subsequently incorporated into appropriate RISC.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Bartel, D. P. (2004). MicroRNAs: genomics, biogenesis, mechanism, and function. *Cell* 116:281-297.
Bertrand, E. et al. (1997). The expression cassette determines the functional activity of ribozymes in mammalian cells by controlling their intracellular localization. *RNA* 3:75-88.
Birmingham, A. et al. (2006). 3' UTR seed matches, but not overall identity, are associated with RNAi off-targets. *Nat Methods* 3:199-204.
Chalk, A. M. et al. (2004). Improved and automated prediction of effective siRNA. *Biochem Biophys Res Commun* 319:264-274.
Doench, J. G. et al. (2003). siRNAs can function as miRNAs. *Genes Dev* 17:438-442.
Eckstein, F. (2000). Phosphorothioate oligodeoxynucleotides: what is their origin and what is unique about them? *Antisense Nucleic Acid Drug Dev* 10:117-21.
Filipowicz, W. et al. (2005). Post-transcriptional gene silencing by siRNAs and miRNAs. *Curr Opin Struct Biol* 75:331-341.
Good, P. D. et al. (1997). Expression of small, therapeutic RNAs in human cell nuclei. *Gene Ther* 4:45-54.
Griffiths-Jones, S. et al. (2006). miRBase: microRNA sequences, targets and gene nomenclature. *Nucleic Acids Res*, 34, D140-144.
Haele, B. S. et al. (2005). siRNA target site secondary structure predictions using local stable substructures. *Nucleic Acids Res* 33(3):e30.
Hannon, G. J. and Rossi, J. J. (2004). Unlocking the potential of the human genome with RNA interference. *Nature* 431:371-378.
Herdewijn, P. (2000). Heterocyclic modifications of oligonucleotides and antisense technology. *Antisense Nucleic Acid Drug Dev* 10:297-310.
Hossbach, M. et al. (2006). Gene silencing with siRNA duplexes composed of target-mRNA-complementary and partially palindromic or partially complementary single-stranded siRNAs. *RNA Biol* 3:82-89.
Kim, V. N. (2005). Small RNAs: classification, biogenesis, and function. *Mol Cells* 79:1-15.
Kreuter, J. (1991). Nanoparticles-preparation and applications. In: *Microcapsules and nanoparticles in medicine and pharmacy*, Donbrow M., ed, CRC Press, Boca Raton, Fla., pp. 125-14.
Lim, L. P. et al. (2005). Microarray analysis shows that some microRNAs downregulate large numbers of target mRNAs. *Nature* 433:769-773.
Liu, J. et al. (2005). MicroRNA-dependent localization of targeted mRNAs to mammalian P-bodies. *Nat Cell Biol* 7:719-723.

Paddison, P. J. et al. (2002). Short hairpin RNAs (shRNAs) induce sequence-specific silencing in mammalian cells. *Genes Dev* 16:948-958.

Rajewsky, N. (2006). microRNA target predictions in animals. *Nat Genet.* 38 Suppl:S8-13.

Rusckowski, M. et al. (2000). Biodistribution and metabolism of a mixed backbone oligonucleotide (GEM 231) following single and multiple dose administration in mice. *Antisense Nucleic Acid Drug Dev* 10:333-345.

Saetrom, P. (2004). Predicting the efficacy of short oligonucleotides in antisense and RNAi experiments with boosted genetic programming. *Bioinformatics* 20:3055-3063.

Saetrom, P. and Snove, O., Jr. (2004). A comparison of siRNA efficacy predictors. Biochem *Biophys Res Commun* 321: 247-253.

Saetrom, P. et al. (2007). Manuscript submitted.

Snove, O. and Rossi, J. J. (2006). Expressing short hairpin RNAs in vivo. *Nature Methods* 3:689-695.

Stein, D. A. et al. (2001) Inhibition of Vesivirus infections in mammalian tissue culture with antisense morpholino oligomers. *Antisense Nucleic Acid Drug Dev* 11:317-25.

Verma, S. And Eckstein, F. (1998). Modified oligonucleotides: synthesis and strategy for users. *Annu Rev Biochem* 67:99-134.

Vert, J. P. et al. (2006). An accurate and interpretable model for siRNA efficacy prediction. *BMC Bioinformatics* 7:520 (17 pages).

Vorobjev, P. E. et al. (2001). Nuclease resistance and RNase H sensitivity of oligonucleotides bridged by oligomethylene-diol and oligoethylene glycol linkers. *Antisense Nucleic Acid Drug Dev* 11:77-85.

Wu, L. et al. (2006). MicroRNAs direct rapid deadenylation of mRNA. *Proc Natl Acad Sci USA* 103:4034-4039.

Zeng, Y. et al. (2002). Both natural and designed micro RNAs can inhibit the expression of cognate mRNAs when expressed in human cells. *Mol Cell* 9:1327-1333.

---

What is claimed is:

1. A multi-targeting RNA molecule that targets two or more different desired target sequences, wherein the RNA molecule comprises a first strand having a 5' terminus and a 3' terminus and a second strand having a 5' terminus and a 3' terminus, wherein the first strand is perfectly complementary to a desired mRNA target sequence, wherein the second strand contains two or more seed matches optimally spaced in a desired 3' UTR containing target gene, wherein the first strand and second strand are not completely complementary and wherein the first strand and the second strand hybridize to form a double stranded RNA molecule, wherein the double stranded RNA molecule is a single duplex.

2. The multi-targeting RNA molecule of claim 1, wherein the optimal spacing between seed matches is between 13 and 100 nucleotides.

3. The multi-targeting RNA molecule of claim 2, wherein the optimal spacing between seed matches is between 13 and 35 nucleotides.

4. The multi-targeting RNA molecule of claim 1, wherein the first strand results in cleavage of the desired mRNA target sequence and wherein the seed matches result in down-regulation of the desired 3' UTR containing target gene.

5. The multi-targeting RNA molecule of claim 4, wherein the desired mRNA target sequence and the desired 3' UTR containing target gene are the same gene.

6. The multi-targeting RNA molecule of claim 5, wherein the gene is an HIV gene.

7. The multi-targeting RNA molecule of claim 4, wherein the desired mRNA target sequence is a target sequence of a first desired gene and the desired 3' UTR containing target gene is a second desired gene.

8. The multi-targeting RNA molecule of claim 7, wherein the first desired gene is CCR5 and the second desired gene is 3' UTR of HIV.

9. The multi-targeting RNA molecule of claim 8, wherein the first strand and the second strand have the nucleotide sequences selected from the following group:

(a)
```
                                            (SEQ ID NO: 46)
first strand: 5' uccaaucugcuugaagacuagggauuc 3'
and
                                            (SEQ ID NO: 45)
second strand: 5' uucccagucaaaaguccaauugga 3';
```

(b)
```
                                            (SEQ ID NO: 48)
first strand: 5' cgcucgggagccucuugcuggaagaua 3'
and
                                            (SEQ ID NO: 47)
second strand: ; 5' uucccagucaaaaguccacgagctg 3'
```

(c)
```
                                            (SEQ ID NO: 50)
first strand: 5' aaaccugaagcucucuucguggggcu 3'
and
                                            (SEQ ID NO: 49)
second strand: 5' uucccagucaaaaguccaagguuu 3';
and
```

(d)
```
                                            (SEQ ID NO: 52)
first strand: 5' ggauaucugaccccuggcccuggugugu 3'
and
                                            (SEQ ID NO: 51)
second strand: 5' uucccagucaaaaguccaauaucc 3'.
```

10. A composition comprising a therapeutically effective amount of the multi-targeting RNA molecule of claim 1 and a pharmaceutically acceptable carrier.

* * * * *

SEQUENCE LISTING

```
<160> NUMBER OF SEQ ID NOS: 56

<210> SEQ ID NO 1
<211> LENGTH: 18
<212> TYPE: RNA
<213> ORGANISM: Artificial
<220> FEATURE:
<223> OTHER INFORMATION: siRNA sense strand

<400> SEQUENCE: 1
ucaggaguau acugcauu                                                       18

<210> SEQ ID NO 2
<211> LENGTH: 19
<212> TYPE: RNA
<213> ORGANISM: Artificial
<220> FEATURE:
<223> OTHER INFORMATION: siRNA antisense strand

<400> SEQUENCE: 2
uguccuucau augacguaa                                                      19

<210> SEQ ID NO 3
<211> LENGTH: 19
<212> TYPE: RNA
<213> ORGANISM: Artificial
<220> FEATURE:
<223> OTHER INFORMATION: siRNA sense strand

<400> SEQUENCE: 3
gagcuucagg uuuggggaa                                                      19

<210> SEQ ID NO 4
<211> LENGTH: 19
<212> TYPE: RNA
<213> ORGANISM: Artificial
<220> FEATURE:
<223> OTHER INFORMATION: siRNA antisense strand

<400> SEQUENCE: 4
cucgaagucc aaaccccuu                                                      19

<210> SEQ ID NO 5
<211> LENGTH: 19
<212> TYPE: RNA
<213> ORGANISM: Artificial
```

```
<220> FEATURE:
<223> OTHER INFORMATION: siRNA sense strand

<400> SEQUENCE: 5
uggacuuuug acugggggaa                                                    19

<210> SEQ ID NO 6
<211> LENGTH: 19
<212> TYPE: RNA
<213> ORGANISM: Artificial
<220> FEATURE:
<223> OTHER INFORMATION: siRNA antisense strand

<400> SEQUENCE: 6
accugaaaac ugacccuu                                                      19

<210> SEQ ID NO 7
<211> LENGTH: 19
<212> TYPE: RNA
<213> ORGANISM: Artificial
<220> FEATURE:
<223> OTHER INFORMATION: siRNA sense strand

<400> SEQUENCE: 7 uucccccauuu agugggggaa                                                   19

<210> SEQ ID NO 8
<211> LENGTH: 19
<212> TYPE: RNA
<213> ORGANISM: Artificial
<220> FEATURE:
<223> OTHER INFORMATION: siRNA antisense strand

<400> SEQUENCE: 8 aaggguaaa ucacccuu                                                       19

<210> SEQ ID NO 9
<211> LENGTH: 19
<212> TYPE: RNA
<213> ORGANISM: Artificial
<220> FEATURE:
<223> OTHER INFORMATION: siRNA sense strand

<400> SEQUENCE: 9
gagaggaguc agagagaau                                                     19

<210> SEQ ID NO 10
<211> LENGTH: 19
<212> TYPE: RNA
<213> ORGANISM: Artificial
<220> FEATURE:
<223> OTHER INFORMATION: siRNA antisense strand

<400> SEQUENCE: 10
cucuccucag ucucucuua                                                     19

<210> SEQ ID NO 11
<211> LENGTH: 19
<212> TYPE: RNA
<213> ORGANISM: Artificial
<220> FEATURE:
<223> OTHER INFORMATION: siRNA sense strand

<400> SEQUENCE: 11
aguccaaucu augacauca                                                     19
```

```
<210> SEQ ID NO 12
<211> LENGTH: 19
<212> TYPE: RNA
<213> ORGANISM: Artificial
<220> FEATURE:
<223> OTHER INFORMATION: siRNA antisense strand

<400> SEQUENCE: 12
ucagguuaga uacuguagu                                                    19

<210> SEQ ID NO 13
<211> LENGTH: 19
<212> TYPE: RNA
<213> ORGANISM: Artificial
<220> FEATURE:
<223> OTHER INFORMATION: siRNA sense strand

<400> SEQUENCE: 13
ucugguuugc agagcuuga                                                    19

<210> SEQ ID NO 14
<211> LENGTH: 19
<212> TYPE: RNA
<213> ORGANISM: Artificial
<220> FEATURE:
<223> OTHER INFORMATION: siRNA antisense strand

<400> SEQUENCE: 14
agaccaaacg ucucgaacu                                                    19

<210> SEQ ID NO 15
<211> LENGTH: 18
<212> TYPE: RNA
<213> ORGANISM: Artificial
<220> FEATURE:
<223> OTHER INFORMATION: siRNA sense strand

<400> SEQUENCE: 15
gugucgaaau gagaagaa                                                     18

<210> SEQ ID NO 16
<211> LENGTH: 19
<212> TYPE: RNA
<213> ORGANISM: Artificial
<220> FEATURE:
<223> OTHER INFORMATION: siRNA antisense strand

<400> SEQUENCE: 16
ccacagcuuu acucuucuu                                                    19

<210> SEQ ID NO 17
<211> LENGTH: 19
<212> TYPE: RNA
<213> ORGANISM: Artificial
<220> FEATURE:
<223> OTHER INFORMATION: siRNA sense strand

<400> SEQUENCE: 17
aagaguggug cagagagaa                                                    19

<210> SEQ ID NO 18
<211> LENGTH: 19
<212> TYPE: RNA
<213> ORGANISM: Artificial
<220> FEATURE:
<223> OTHER INFORMATION: siRNA sense strand
```

```
<400> SEQUENCE: 18
ucaggaagua uacugcauu                                                    19

<210> SEQ ID NO 19
<211> LENGTH: 19
<212> TYPE: RNA
<213> ORGANISM: Artificial
<220> FEATURE:
<223> OTHER INFORMATION: siRNA sense strand

<400> SEQUENCE: 19
gagcuucagg uuugggaa                                                     19

<210> SEQ ID NO 20
<211> LENGTH: 19
<212> TYPE: RNA
<213> ORGANISM: Artificial
<220> FEATURE:
<223> OTHER INFORMATION: siRNA sense strand

<400> SEQUENCE: 20
gcccgaagga auagaagaa                                                    19

<210> SEQ ID NO 21
<211> LENGTH: 19
<212> TYPE: RNA
<213> ORGANISM: Artificial
<220> FEATURE:
<223> OTHER INFORMATION: siRNA sense strand

<400> SEQUENCE: 21
acauauuggg gucugcaua                                                    19

<210> SEQ ID NO 22
<211> LENGTH: 19
<212> TYPE: RNA
<213> ORGANISM: Artificial
<220> FEATURE:
<223> OTHER INFORMATION: siRNA sense strand

<400> SEQUENCE: 22
ggaacaagcc ccagaagac                                                    19

<210> SEQ ID NO 23
<211> LENGTH: 21
<212> TYPE: RNA
<213> ORGANISM: Artificial
<220> FEATURE:
<223> OTHER INFORMATION: siRNA oligonucleotide

<400> SEQUENCE: 23
uagacacgca aggagacaug c                                                 21

<210> SEQ ID NO 24
<211> LENGTH: 21
<212> TYPE: RNA
<213> ORGANISM: Artificial
<220> FEATURE:
<223> OTHER INFORMATION: siRNA oligonucleotide

<400> SEQUENCE: 24
uuguuuccuu gggugaauag a                                                 21

<210> SEQ ID NO 25
```

```
<211> LENGTH: 25
<212> TYPE: DNA
<213> ORGANISM: Artificial
<220> FEATURE:
<223> OTHER INFORMATION: siRNA oligonucleotide
<220> FEATURE:
<221> NAME/KEY: misc_feature
<222> LOCATION: (24)..(25)
<223> OTHER INFORMATION: DNA bases

<400> SEQUENCE: 25
uagacacgca aggagacaug cccag                                              25

<210> SEQ ID NO 26
<211> LENGTH: 27
<212> TYPE: RNA
<213> ORGANISM: Artificial
<220> FEATURE:
<223> OTHER INFORMATION: siRNA oligonucleotide

<400> SEQUENCE: 26
cugggcuugu uccuugggu gaauaga                                             27

<210> SEQ ID NO 27
<211> LENGTH: 27
<212> TYPE: RNA
<213> ORGANISM: Artificial
<220> FEATURE:
<223> OTHER INFORMATION: siRNA oligonucleotide

<400> SEQUENCE: 27
uagacacgca aggagacaug ccucuag                                            27

<210> SEQ ID NO 28
<211> LENGTH: 27
<212> TYPE: RNA
<213> ORGANISM: Artificial
<220> FEATURE:
<223> OTHER INFORMATION: siRNA oligonucleotide

<400> SEQUENCE: 28
cugggcuucu uccuugggu gaauaga                                             27

<210> SEQ ID NO 29
<211> LENGTH: 27
<212> TYPE: RNA
<213> ORGANISM: Artificial
<220> FEATURE:
<223> OTHER INFORMATION: siRNA oligonucleotide

<400> SEQUENCE: 29
uuuagacacg caaggagaca ugccucu                                            27

<210> SEQ ID NO 30
<211> LENGTH: 27
<212> TYPE: RNA
<213> ORGANISM: Artificial
<220> FEATURE:
<223> OTHER INFORMATION: siRNA oligonucleotide

<400> SEQUENCE: 30
cugggcuugu uccuugggu gaauaga                                             27

<210> SEQ ID NO 31
<211> LENGTH: 21
<212> TYPE: RNA
<213> ORGANISM: Artificial
```

<220> FEATURE:
<223> OTHER INFORMATION: siRNA oligonucleotide

<400> SEQUENCE: 31
gcagacuaaa gucaagucau g        21

<210> SEQ ID NO 32
<211> LENGTH: 21
<212> TYPE: RNA
<213> ORGANISM: Artificial
<220> FEATURE:
<223> OTHER INFORMATION: siRNA oligonucleotide

<400> SEQUENCE: 32
ugaacuugac aauaucugcu c        21

<210> SEQ ID NO 33
<211> LENGTH: 25
<212> TYPE: DNA
<213> ORGANISM: Artificial
<220> FEATURE:
<223> OTHER INFORMATION: siRNA oligonucleotide
<220> FEATURE:
<221> NAME/KEY: misc_feature
<222> LOCATION: (24)..(25)
<223> OTHER INFORMATION: DNA bases

<400> SEQUENCE: 33
gcagacuaaa gucaagucau ggcct        25

<210> SEQ ID NO 34
<211> LENGTH: 27
<212> TYPE: RNA
<213> ORGANISM: Artificial
<220> FEATURE:
<223> OTHER INFORMATION: siRNA oligonucleotide

<400> SEQUENCE: 34
aggccaugaa cuugacaaua ucugcuc        27

<210> SEQ ID NO 35
<211> LENGTH: 27
<212> TYPE: RNA
<213> ORGANISM: Artificial
<220> FEATURE:
<223> OTHER INFORMATION: siRNA oligonucleotide

<400> SEQUENCE: 35
gcagacuaaa gucaagucag aacuuuu        27

<210> SEQ ID NO 36
<211> LENGTH: 27
<212> TYPE: RNA
<213> ORGANISM: Artificial
<220> FEATURE:
<223> OTHER INFORMATION: siRNA oligonucleotide

<400> SEQUENCE: 36
aggccaugaa cuugacaaua ucugcuc        27

<210> SEQ ID NO 37
<211> LENGTH: 27
<212> TYPE: RNA
<213> ORGANISM: Artificial
<220> FEATURE:
<223> OTHER INFORMATION: siRNA oligonucleotide

<400> SEQUENCE: 37
uugcagacua aagucaaguc agaacuu                                              27

<210> SEQ ID NO 38
<211> LENGTH: 27
<212> TYPE: RNA
<213> ORGANISM: Artificial
<220> FEATURE:
<223> OTHER INFORMATION: siRNA oligonucleotide

<400> SEQUENCE: 38
aggccaugaa cuugacaaua ucugcuc                                              27

<210> SEQ ID NO 39
<211> LENGTH: 25
<212> TYPE: DNA
<213> ORGANISM: Artificial
<220> FEATURE:
<223> OTHER INFORMATION: siRNA oligonucleotide
<220> FEATURE:
<221> NAME/KEY: misc_feature
<222> LOCATION: (24)..(25)
<223> OTHER INFORMATION: DNA bases

<400> SEQUENCE: 39
gggcaaucuc aucuuccgac ccgtc                                                25

<210> SEQ ID NO 40
<211> LENGTH: 27
<212> TYPE: RNA
<213> ORGANISM: Artificial
<220> FEATURE:
<223> OTHER INFORMATION: siRNA oligonucleotide

<400> SEQUENCE: 40
gacgggucug aaguugagau ucugcua                                              27

<210> SEQ ID NO 41
<211> LENGTH: 19
<212> TYPE: RNA
<213> ORGANISM: Artificial
<220> FEATURE:
<223> OTHER INFORMATION: siRNA sense strand

<400> SEQUENCE: 41
aucccuaguc uucaagcag                                                       19

<210> SEQ ID NO 42
<211> LENGTH: 20
<212> TYPE: RNA
<213> ORGANISM: Artificial
<220> FEATURE:
<223> OTHER INFORMATION: siRNA sense strand

<400> SEQUENCE: 42
uuuuccagca agaggcuccc                                                      20

<210> SEQ ID NO 43
<211> LENGTH: 20
<212> TYPE: RNA
<213> ORGANISM: Artificial
<220> FEATURE:
<223> OTHER INFORMATION: siRNA sense strand

<400> SEQUENCE: 43
cccaccagaa gagagcuuca                                                      20

<210> SEQ ID NO 44
<211> LENGTH: 20
<212> TYPE: RNA
<213> ORGANISM: Artificial
<220> FEATURE:
<223> OTHER INFORMATION: siRNA sense strand

<400> SEQUENCE: 44
acaccagggc caggggucag                                               20

<210> SEQ ID NO 45
<211> LENGTH: 25
<212> TYPE: RNA
<213> ORGANISM: Artificial
<220> FEATURE:
<223> OTHER INFORMATION: siRNA U2 anti-sense strand

<400> SEQUENCE: 45
uuccccaguc aaaaguccaa uugga                                         25

<210> SEQ ID NO 46
<211> LENGTH: 27
<212> TYPE: RNA
<213> ORGANISM: Artificial
<220> FEATURE:
<223> OTHER INFORMATION: siRNA reverse-complementary

<400> SEQUENCE: 46
uccaaucugc uugaagacua gggauuc                                       27

<210> SEQ ID NO 47
<211> LENGTH: 25
<212> TYPE: RNA
<213> ORGANISM: Artificial
<220> FEATURE:
<223> OTHER INFORMATION: siRNA U2 anti-sense strand

<400> SEQUENCE: 47
uuccccaguc aaaaguccac gagcg                                         25

<210> SEQ ID NO 48
<211> LENGTH: 27
<212> TYPE: RNA
<213> ORGANISM: Artificial
<220> FEATURE:
<223> OTHER INFORMATION: siRNA reverse-complementary

<400> SEQUENCE: 48
cgcucgggag ccucuugcug gaagaua                                       27

<210> SEQ ID NO 49
<211> LENGTH: 25
<212> TYPE: RNA
<213> ORGANISM: Artificial
<220> FEATURE:
<223> OTHER INFORMATION: siRNA U2 anti-sense strand

<400> SEQUENCE: 49
uuccccaguc aaaaguccaa gguuu                                         25

<210> SEQ ID NO 50
<211> LENGTH: 28
<212> TYPE: RNA
<213> ORGANISM: Artificial
<220> FEATURE:

<223> OTHER INFORMATION: siRNA reverse-complementary

<400> SEQUENCE: 50
aaaccugaag cucucuucug gugggcu                                28

<210> SEQ ID NO 51
<211> LENGTH: 25
<212> TYPE: RNA
<213> ORGANISM: Artificial
<220> FEATURE:
<223> OTHER INFORMATION: siRNA U2 anti-sense strand

<400> SEQUENCE: 51
uuccccaguc aaaaguccaa uaucc                                 25

<210> SEQ ID NO 52
<211> LENGTH: 28
<212> TYPE: RNA
<213> ORGANISM: Artificial
<220> FEATURE:
<223> OTHER INFORMATION: siRNA reverse-complementary

<400> SEQUENCE: 52
ggauaucuga ccccuggccc uggugugu                              28

<210> SEQ ID NO 53
<211> LENGTH: 22
<212> TYPE: RNA
<213> ORGANISM: Artificial
<220> FEATURE:
<223> OTHER INFORMATION: siRNA target

<400> SEQUENCE: 53
ggccugggcg ggacugggga gu                                    22

<210> SEQ ID NO 54
<211> LENGTH: 19
<212> TYPE: RNA
<213> ORGANISM: Artificial
<220> FEATURE:
<223> OTHER INFORMATION: siRNA miRNA

<400> SEQUENCE: 54
uuccccagcu cucccaggc                                        19

<210> SEQ ID NO 55
<211> LENGTH: 27
<212> TYPE: RNA
<213> ORGANISM: Artificial
<220> FEATURE:
<223> OTHER INFORMATION: siRNA target

<400> SEQUENCE: 55
ugcuacaagg gacuuuccgc ugggac                                27

<210> SEQ ID NO 56
<211> LENGTH: 19
<212> TYPE: RNA
<213> ORGANISM: Artificial
<220> FEATURE:
<223> OTHER INFORMATION: siRNA miRNA

<400> SEQUENCE: 56
uuccccagcu cucccaggc                                        19